(12) United States Patent
Wu (10) Patent No.: US 8,058,063 B2
(45) Date of Patent: Nov. 15, 2011

(54) METHOD OF PRODUCING REGION-SPECIFIC NEURONS FROM HUMAN NEURONAL STEM CELLS

(75) Inventor: Ping Wu, League City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1927 days.

(21) Appl. No.: 10/176,971

(22) Filed: Jun. 19, 2002

(65) Prior Publication Data

US 2003/0013193 A1  Jan. 16, 2003

Related U.S. Application Data

(60) Provisional application No. 60/300,344, filed on Jun. 22, 2001.

(51) Int. Cl.
*C12N 5/02* (2006.01)
(52) U.S. Cl. ........ 435/377; 435/384; 435/402; 424/93.7
(58) Field of Classification Search .................. None
See application file for complete search history.

(56) References Cited

U.S. PATENT DOCUMENTS

| 5,750,376 | A | * | 5/1998 | Weiss et al. | ................ | 435/69.52 |
| 5,968,829 | A | * | 10/1999 | Carpenter | ..................... | 435/467 |
| 6,294,359 | B1 | | 9/2001 | Fiddes et al. | | |
| 6,399,369 | B1 | | 6/2002 | Weiss et al. | | |

OTHER PUBLICATIONS

Principles of Neural Sciences (1991) Ch 17, pp. 248-249, and publisher and copyright page.*
Daley et al (2003). Hematology. 398-418.*
Kalyani et al (1998). J. Neurosci. 18, 7856-7868.*
Whittemore et al. (1999). Experimental Cell Research. 252, 75-95.*
Barami et al. (2001). Neurological Res. 23, 260-266.*
Blackshaw and Cepko, "Stem Cells that know their place," *Nature Neuroscience*, Dec. 2002;5(12):1251-1252.
Gao et al., "Human Neural Stem Cell-Derived Cholinergic Neurons Innervate Muscle in Motoneuron Deficient Adult Rats," *Neuroscience*, 2005;131:257-262.
Hofstetter et al., "Marrow stromal cells form guiding strands in the injured spinal cord and promote recovery," *PNAS*, Feb. 19, 2002;99(4):2199-2204.
Ogawa et al., "Transplantation of In Vitro-Expanded Fetal Neural Progenitor Cells Results in Neurogenesis and Functional Recovery After Spinal Cord Contusion Injury in Adult Rats," *Journal of Neuroscience Research*, Sep. 15, 2002;69(6):925-933.
Schmalbruch, "Motoneuron Death After Sciatic Nerve Section in Newborn Rats," *Journal of Comparative Neurology*, 1984;224:252-258.
Shihabuddin et al., "Adult Spinal Cord Stem Cells Generate Neurons after Transplantation in the Adult Dentate Gyrus," *Journal of Neuroscience*, Dec. 1, 2000, 20(23):8727-8735.
Snider et al., "Axotomy-Induced Neuronal Death during Development," *Journal of Neurobiology*, 1992;23(9):1231-1246.

Tarasenko et al., "Effect of Growth Factors on Proliferation and Phenotypic Differentiation of Human Fetal Neural Stem Cells," *Journal of Neuroscience Research*, 2004;78:625-636. Published online Oct. 15, 2004.
Vroemen et al., "Adult neural progenitor cell grafts survive after acute spinal cord injury and integrate along axonal pathways," *European Journal of Neuroscience*, 2003;18:743-751.
Wu et al., "Region-Specific generation of cholinergic neurons from fetal human neural stem cells grafted in adult rat," *Nature Neuroscience*, Dec. 2002;5(12):1271-1278.
Emerich et al., "Transplantation of Fetal Cholinergic Neurons Into the Hippocampus Attenuates the Cognitive and Neurochemical Deficits Induced by AF64A," *Brain Research Bulletin*, 1992; 28:219-226.
Gao et al., "Transplantation of primed human fetal neural stem cells improves cognitive function in rats after traumatic brain injury," *Experimental Neurology*, 2006; 201:281-292.
Ikegami et al., "Transplantation of ventral forebrain cholinergic neurons to the hippocampus ameliorates impairment of radial-arm maze learning in rats with AF64A treatment," *Brain Research*, 1991; 548:187-195.
Kalyani et al., "Neuroepithelial Stem Cells from Embryonic Spinal Cord: Isolation, Characterization, and Clonal Analysis," *Developmental Biology*, 1997; 186:202-223.
Lindvall et al., "Stem cell therapy for human neurodegenerative disorders—how to make it work," *Nature Medicine*, 2004;10:S42-S50.
Ronghao et al., "Motoneuron Differentiation of Immortalized Human Spinal Cord Cell Lines, "*Journal of Neuroscience Research*, 2000; 59:342-352.
Tarasenko et al., "Human fetal neural stem cells grafted into contusion-injured rat spinal cords improve behavior," *Journal of Neuroscience Research*, 2007; 85:47-57.
Wright et al., "Human progenitor cells isolated from the developing cortex undergo decreased neurogenesis and eventual senescence following expansion in vitro," *Experimental Cell Research*, 2006; 312:2107-2120.
Anderson, "Stem cells and pattern formation in the nervous system: the possible versus the actual," *Neuron*. Apr. 2001:30(1):19-35.
Armstrong et al., "Neural stem cells: from cell biology to cell replacement," *Cell Transplant*. Mar.-Apr. 2000:9(2):139-52.
Barzu et al., "Heparin-derived oligosaccharides: affinity for acidic fibroblast growth factor and effect on its growth-promoting activity for human endothelial cells." *J Cell Physiol*. Sep. 1989:140(3):538-48. Basilico et al., "The FGF family of growth factors and oncogenes." *Adv Cancer Res*. 1992:59:115-65.
Bonfanti et al., "Multipotent stem cells in the adult central nervous system," Stem cells and CNS Development, Rao, M.S. (ed.), Humana Press, Totowa, NJ 2001; 49-70.
Bottenstein et al.. "Growth of a rat neuroblastoma cell line in serum-free supplemented medium." *Proc Natl Acad Sci U S A*. Jan. 1979;76(1):514-7.

(Continued)

*Primary Examiner* — Daniel E Kolker
(74) *Attorney, Agent, or Firm* — Mueting, Raasch & Gebhardt, P.A.

(57) ABSTRACT

A method of priming neural stem cells in vitro by adhesively culturing in a mixture of basic fibroblast growth factor, laminin and heparin to differentiate into specific neuronal phenotypes, including cholinergic, glutamatergic and GABAergic neurons, in a region-specific manner, when transplanted in vivo.

41 Claims, 5 Drawing Sheets

OTHER PUBLICATIONS

Brustle et al.. "Chimeric brains generated by intraventricular transplantation of fetal human brain cells into embryonic rats." *Nat Biotechnol*. Nov. 1998;16(11): 1040-4.

Caldwell et al., "Growth factors regulate the survival and fate of cells derived from human neurospheres." *Nat Biotechnol*. May 2001:19(5):475-9.

Cao et al., "Pluripotent stem cells engrafted into the normal or lesioned adult rat spinal cord are restricted to a glial lineage." *Exp Neurol*. Jan. 2001;167(1):48-58.

Carpenter et al., "In vitro expansion of a multipotent population of human neural progenitor cells," *Exp Neurol*. Aug. 1999;158(2):265-78.

Esch et al., "Primary structure of bovine pituitary basic fibroblast growth factor (FGF) and comparison with the amino-terminal sequence of bovine brain acidic FGF," *Proc Natl Acad Sci U S A*. Oct. 1985;82(19):6507-11.

Fannon et al., "Potentiation and inhibition of bFGF binding by heparin: a model for regulation of cellular response," *Biochemistry*. Feb. 15, 2000;39(6):1434-45.

Fernig et al., "Fibroblast growth factors and their receptors: an information network controlling tissue growth, morphogenesis and repair," *Prog Growth Factor Res*. 1994;5(4):353-77.

Flax et al., "Engraftable human neural stem cells respond to developmental cues, replace neurons, and express foreign genes," *Nat Biotechnol*. Nov. 1998;16(11): 1033-9.

Fricker et al., "Site-specific migration and neuronal differentiation of human neural progenitor cells after transplantation in the adult rat brain," *J Neurosci*. Jul. 15, 1999;19(14):5990-6005.

Gage, "Mammalian neural stem cells," *Science*. Feb. 25, 2000;287(5457):1433-8.

Gospodarowicz et al., "Bovine brain and pituitary fibroblast growth factors: comparison of their abilities to support the proliferation of human and bovine vascular endothelial cells," *J Cell Biol*. Dec. 1983;97(6):1677-85.

Gospodarowicz et al., "Isolation of pituitary fibroblast growth factor by fast protein liquid chromatography (FPLC): partial chemical and biological characterization," *J Cell Physiol*. Feb. 1985:122(2):323-32.

Gospodarowicz et al., "Effect of fibroblast growth factor and lipoproteins on the proliferation of endothelial cells derived from bovine adrenal cortex, brain cortex, and corpus luteum capillaries." *J Cell Physiol*. Apr. 1986;127(1):121-36.

Isacson et al.. "Neural transplantation studies reveal the brain's capacity for continuous reconstruction." *Trends Neurosci*. Oct. 1997:20(10):477-82.

Jessell, "Neuronal specification in the spinal cord: inductive signals and transcriptional codes," *Nat Rev Gent*.Oct. 2000:1(1):20-9.

Johansson et al., "Neural stem cells in the adult human brain," *Exp Cell Res*. Dec. 15, 1999:253(2):733-6.

Kan et al., "An essential heparin-binding domain in the fibroblast growth factor receptor kinase." *Science*. Mar. 26, 1993;259(5103):1918-21.

Messam et al., "Coexpression of nestin in neural and glial cells in the developing human CNS defined by a human-specific anti-nestin antibody," *Exp Neural*. Feb. 2000;161(2):585-96.

Ornitz et al., "Receptor specificity of the fibroblast growth factor family," *J Biol Chem*. Jun. 21, 1996;271(25):15292-7.

Ostenfeld et al., "Human neural precursor cells express low levels of telomerase in vitro and show diminishing cell proliferation with extensive axonal outgrowth following transplantation," *Exp Neurol*. Jul. 2000;164 6-(1):215-26.

Palmer et al., "Cell culture. Progenitor cells from human brain after death," *Nature*. May 3, 2001;411(6833):42-3.

Potten et al., "Stem cells: attributes, cycles, spirals, pitfalls and uncertainties. Lessons for and from the crypt," *Development* 1990 110(4):1001-20.

Reubinoff et al., "Neural progenitors from human embryonic stem cells." *Nat Biotechnol*. Dec. 2001: 19(12):1134-40.

Roy et al., "In vitro neurogenesis by progenitor cells isolated from the adult human hippocampus." *Nat Med*. Mar. 2000:6(3):271-7.

Schmitz et al., "GFP associates with microfilaments in fixed cells." *Histochem Cell Biol*. Jul. 2001:116(1):89-94.

Shamblott et al., "Derivation of pluripotent stem cells from cultured human primordial germ cells." *Proc. Natl Acad U S A*. Nov. 10, 1998;95(23): 13726-31.

Shamblott et al., "Correction for Derivation of pluripotent stem cells from cultured human primoridal germ cells" *PNAS Online*: [online] retrieved on Jul. 3, 2002. Retrieved from the Internet<URL:http://www/pnas.org/egi/content/full/96/3/1162/c>: 1 pg.

Sheen et al., "Neural precursor differentiation following transplantation into neocortex is dependent on intrinsic developmental state and receptor competence." *Exp Neurol*. Jul. 1999:158(1):47-62.

Shihabuddin et al., "Stem cell technology for basic science and clinical applications." *Arch Neurol*. Jan. 1999;56(1):29-32.

Shihabuddin et al., "Adult spinal cord stem cells generate neurons after transplantation in the adult dentate gyrus," . *J Neurosci*. Dec. 1, 2000;20(23): 8727-35.

Smithies et al., "Insertion of DNA sequences into the human chromosomal beta-globin locus by homologous recombination," *Nature*. Sep. 19-25, 1985;317 (6034):230-4.

Song et al., "Astroglia induce neurogenesis from adult neural stem cells," *Nature*. May 2, 2002:417(6884):39-44.

"Stem Cells: A Primer." *National Institutes of Health*, May 2000; [online] retrieved on Sep. 16, 2002. Retrieved from the Internet: <URL: http://www.nih.gov/news/stemcell/primer.htm>:6 pgs.

Suhonen et al., "Differentiation of adult hippocampus-derived progenitors into olfactory neurons in vivo," Nature. Oct. 17, 1996;383(6601):624-7.

Svendsen et al.. "Long-term survival of human central nervous system progenitor cells transplanted into a rat model of Parkinson's disease." *Exp Neurol*. Nov. 1997:148(1):135-46.

Svendsen et al., "A new method for the rapid and long term growth of human neural precursor cells," *J Neurosci Methods*. Dec. 1, 1998:85(2):141-52.

Terada et al.. "Bone marrow cells adopt the phenotype of other cells by spontaneous cell fusion." *Nature*. Apr. 4, 2002:416(6880):542-5.

Thomson et al.. "Embryonic stem cell lines derived from human blastocysts," *Science*. Nov. 6, 1998:282(5391):1145-7.

Uchida et al., "Direct isolation of human central nervous system stem cells." *Proc. Natl Acad Sci U S A*. Dec. 19, 2000:9¯(26):14720-5.

Vescovi et al., "Isolation and cloning of multipotential stem cells from the embryonic human CNS and establishment of transplantable human neural stem cell lines by epigenetic stimulation." *Exp Neurol*. Mar. 1999;156(1):71-83.

Villa et al., "Establishment and properties of a growth factor-dependent, perpetual neural stem cell line from the human CNS." *Exp Neurol*. Jan. 2000:161(1):67-84.

Whittemore et al., "Mitogen and substrate differentially affect the lineage restriction of adult rat subventricular zone neural precursor cell populations," *Exp Cell Res*. Oct. 10, 1999:252(1):75-95.

Wu et al., "Transduction of human neural progenitor cells using recombinant adeno-associated viral vectors," *Gene Ther*. Feb. 2002;9(4):245-55.

Wu et al., "Generation of cholinergic neurons from human neural stem cells." *Journal of Neurochemistry*: Jun. 2002:81(Suppl. 1): Abstract No. S12-04.

Wu et al., "Region-specific generation of cholinergic neurons from human neural stem cells grafted in adult rat." $28^{th}$ Meeting of the Federation of European Biochemical Societies Israel Society for Biochemistry and Molecular Biology. Istanbul. Turkey. Oct. 20-25, 2002: 269(Suppl. 1): Abstract No. S2.8-2.

Ying, et al., "Changing potency by spontaneous fusion." *Nature*. Apr. 4, 2002:416(6880):545-8.

Zhang et al., "In vitro differentiation of transplantable neural precursors from human embryonic stem cells." *Nat Biotechnol*. Dec. 2001:19(12):1129-33.

Zheng et al., "Fidelity of targeted recombination in human fibroblasts and murine embryonic stem cells." *Proc Natl Acad Sci U S A*. Sep. 15, 1991:88(18):8067-71.

Ciccolini et al., "Local and Global Spontaneous Calcium Events Regulate Neurite Outgrowth and Onset of GABAergic Phenotype during Neural Precursor Differentiation," *The Journal of Neuroscience*, 2003; 23(1):103-111.

Hitoshi et al., "Neural stem cell lineages are regionally specified, but not committed, within distinct compartments of the developing brain," *Development*, 2002; 129:233-244.

International Preliminary Report on Patentability and Written Opinion for PCT/US02/19743 (10 pgs). Jun. 27, 2007.

Jain et al., "GABAergic immunoreactivity is predominant in neurons derived from expanded human neural precursor cells in vitro," *Experimental Neurology*, 2003; 182:113-123.

Li et al., "Specification of motoneurons from human embryonic stem cells," *Nature Biotechnology*, 2005; 23(2):215-221.

Ostenfeld et al., "Regional specification of rodent and human neurospheres," *Developmental Brain Research*, 2002; 134:43-55.

Parmar et al., "Regional specification of neurosphere cultures derived from subregions of the embryonic telencephalon," *Molecular and Cellular Neuroscience*, 2002; 21(4):645-656.

Ray et al., "Differential properties of adult rat and mouse brain-derived neural stem/progenitor cells," *Molecular and Cellular Neuroscience*, 2006; 31:560-573.

Smith et al., "Embryonic Neural Progenitor Cells: The Effects of Species, Region, and Culture Conditions on Long-Term Proliferation and Neuronal Differentiation," *Journal of Hemototherapy & Stem Cell Research*, 2003; 12:713-725.

Wu et al., "Region-Specific Generation of Cholinergic Neurons From Human Neural Stem Cells Grafted in Adult Rat," Society for Neuroscience, 32nd Annual Meeting, Orlando, FL, Nov. 2-7, 2002; 1 page.

* cited by examiner

METHOD OF PRODUCING REGION-SPECIFIC NEURONS FROM HUMAN NEURONAL STEM CELLS

This application claims the benefit of U.S. Provisional Application Ser. No. 60/300,344, filed Jun. 22, 2001, which is incorporated by references herein.

BACKGROUND

Many neurological disorders result from the loss of neurons through disease or injury, and these cells are not intrinsically replaced. Such neurological disorders include neurodegenerative disorders of the CNS, such as Parkinson's disease (PD), Alzheimer's disease (AD), multiple sclerosis, Huntington's disease and amyotrophic lateral sclerosis (ALS or Lou Gehrig's disease). AD and ALS are due to the degeneration of cholinergic neurons. Such neurological disorders also include neurotrauma, such as spinal cord injuries, head injuries and stroke-related dementia. An exciting new strategy for the treatment of such disorders is to replace the damaged or lost neurons by implanting healthy neurons into the affected areas. For example, the implantation of fetal neurons into the brain of PD patients has resulted in the improvement of motor function. A potential therapeutic approach for treating AD, ALS and spinal cord injuries is to replace lost cholinergic neurons by the implantation of new, healthy cholinergic neurons.

Recent progress in the isolation and propagation of human stem cells in culture has generated a potentially unlimited donor source for such treatments. Current advances in the field include the isolation and propagation of human embryonic stem (ES) cells (Thomson et al. *Science* 1998; 282:1145) and germ (EG) cells (Shamblott et al. *PNAS* 1998; 95:13726). These cells are pluripotent, since they can become any cell type in the human body, including neurons. Multipotent neural stem cells have also been isolated successfully from both fetal CNS (see Villa et al. *Exp. Neurol.* 2000; 161:67-84; Carpenter et al. *Exp. Neurol.* 1999; 158:265-278; Svendsen et al. *J. Neurosci. Methods* 1998; 85:141-152); Uchida et al. *PNAS* 2000; 97:14720-14725; and Vescovi et al. *Exp. Neurol.* 1999; 56:71-83) or adult CNS (see Roy et al. *Nat. Med.* 2000; 6:271-277; Johansson et al. *Exp. Cell Res.* 1999; 253:733-736; and Palmer et al. *Nature* 2001; 411:42-43). The capabilities of self-renewal and multipotential differentiation render these stem cells an attractive and presumably unlimited donor source for cell replacement therapy to treat neurological disorders.

While such cells could serve as a source of new neurons to ameliorate many neural disorders, a critical issue is how to direct these pluripotent or multipotent stem cells toward a specific cell lineage in order to meet a desirable therapeutic requirement. For example, treating spinal cord injury, AD or ALS using a cell replacement strategy requires the differentiation of cholinergic neurons from these stem cells. Human or rodent stem cells are able to differentiate into specific neuronal types when grafted into either developing CNS (see Flax et al. *Nat. Biotechnol.* 1998; 16:1033; Brustle et al. *Nat. Biotech.* 1998; 16:1040-1044; Reubinoff et al. *Nat. Biotech.* 2001; 19:1134-1140; and Zhang et al. *Nat. Biotech.* 2001; 19:1129-1133) or neurogenic areas of the adult CNS (see Fricker et al. *J. Neurosci.* 1999; 19:5990-6005; Shihabuddin et al. *J. Neurosci.* 2000; 20:8727-8735; and Suhonen et al. *Nature* 1996; 383:624-627). However, these cells remain undifferentiated or become mainly glial cells when transplanted into non-neurogenic regions of the adult CNS, (see Svendsen et al. *Exp. Neurol.* 1997; 148:135-146; Sheen et al. *Exp. Neurol.* 1999; 158:47-62; Fricker et al. *J. Neurosci.* 1999; 19:5990-6005; Shihabuddin et al. *J. Neurosci.* 2000; 20:8727-8735; and Cao et al. *Exp. Neurol.* 2001; 167: 48-58). This indicates that in vitro priming or differentiation prior to grafting is necessary for these cells to become specific neuronal subtypes such as cholinergic neurons. There have been no reports on the generation of a significant number of cholinergic neurons from long-term mitogen-expanded human stem cells. Such neurons play key roles in motor function as well as learning and memory, and thus are highly relevant to clinical applications. It is a major obstacle that the majority of such cells do not differentiate into cholinergic neurons when grafted into non-neurogenic areas of the adult CNS. See Svendsen et al. *Exp. Neurol.* 1997; 148: 135-146; Sheen et al. *Exp. Neurol.* 1999; 158:47-62; Fricker et al. *J. Neurosci.* 1999; 19: 5990-6005; Shihabuddin et al. *J. Neurosci.* 2000; 20:8727-8735; and Cao et al. *Exp. Neurol.* 2001; 167: 48-58. Thus, there is a need for new methods to direct pluripotent or multipotent stem cells to differentiate into neurons of a specific lineage. For example, there is a need for methods to produce cholinergic neurons from stem cells and/or progeny thereof.

SUMMARY OF THE INVENTION

The present invention includes a method of producing neurons by adhesively culturing neural stem cells and/or progeny thereof in vitro with a mixture including a mitogenic growth factor, a heparin-like agent and an extracellular matrix component, and implanting the cultured stem cells and/or progeny thereof into the mammalian spinal cord or brain, where they differentiate into neurons. The cells may be transplanted into the spinal cord or the medial septum of the brain, for example, where they differentiate into cholinergic neurons. Typically, of the neurons formed, at least 50% are cholinergic neurons. The cells may be transplanted into the prefrontal cortex region of the brain, for example, where they differentiate into glutamatergic neurons. Typically, of the neurons formed, at least 50% are glutamatergic neurons. The cells may also be transplanted into the hippocampus region of the brain, for example, where they differentiate into GABAergic neurons. Typically, of the neurons formed, at least 50% are GABAergic neurons. The stem cells and/or progeny thereof may be multipotent stem cells, pluripotent stem cells, or combinations thereof. The stem cells and/or progeny thereof may be neural stem cells. These stem cells and/or progeny thereof may be derived from embryonic neural tissue, fetal neural tissue, adult neural tissue, or combinations thereof. The mitogenic growth factor may be basic fibroblast growth factor, for example, which may be at a concentration of up to about 20 ng/ml. The heparin-like agent may be heparin, for example, which may be at a concentration of about 0.5 µg/ml to about 10 µg/ml. The extracellular matrix component may be laminin, collagen, fibronectin, or combinations thereof. The extracellular matrix component, for example, may be laminin and, for example, may be present at a concentration of about 0.5 µg/ml to about 5 µg/ml laminin. The stem cells and/or progeny thereof may be cultured adhesively onto a fixed substrate, which may be poly-D-lysine, poly-L-ornithine, laminin, matrigel, collagen or fibronectin, for example. The stem cells and/or progeny thereof may be cultured in vitro for about 5 to 7 days prior to implanting. The culture mixture may further include mammalian Sonic Hedgehog protein or an N-terminus-containing fragment thereof, for example, which may be at a concentration of about 0.002 µg/ml to about 1.0 µg/ml.

The present invention also includes a method of producing neurons, by adhesively culturing neural stem cells and/or progeny thereof in vitro with a mixture including basic fibroblast growth factor, heparin and laminin, and implanting the cultured stem cells and/or progeny thereof into the mammalian spinal cord or brain, where the cells differentiate into neurons.

The present invention further includes a method of producing cholinergic neurons, by adhesively culturing neural stem cells and/or progeny thereof in vitro with a mixture comprising basic fibroblast growth factor, heparin and laminin, and implanting the cultured stem cells and/or progeny thereof into the mammalian spinal cord or medial septum, where they differentiate into cholinergic neurons. Typically, at least 50% of the neurons formed are cholinergic neurons. This mixture may include up to about 20 ng/ml basic fibroblast growth factor, about 0.5 µg/ml to about 5 µg/ml laminin, and 0.5 µg/ml to about 10 µg/ml heparin.

The present invention also includes a method of producing glutamatergic neurons by adhesively culturing neural stem cells and/or progeny thereof in vitro with a mixture including basic fibroblast growth factor, heparin and laminin, and implanting the cultured stem cells and/or progeny thereof into the prefrontal cortex region of the brain, where they differentiate into glutamatergic neurons. Typically, at least 50% of the neurons formed are glutamatergic neurons. This mixture may include, for example, up to about 20 ng/ml basic fibroblast growth factor, about 0.5 µg/ml to about 5 µg/ml laminin, and about 0.5 µg/ml to about 10 µg/ml heparin.

The present invention includes a method of producing GABAergic neurons by adhesively culturing neural stem cells and/or progeny thereof in vitro with a mixture including basic fibroblast growth factor, heparin and laminin, and implanting the cultured stem cells and/or progeny thereof into the hippocampus region of the brain, where they differentiate into GABAergic neurons. Typically, at least 50% of the neurons formed are GABAergic neurons. This mixture may include, for example, up to about 20 ng/ml basic fibroblast growth factor, about 0.5 µg/ml to about 5 µg/ml laminin, and about 0.5 µg/ml to about 10 µg/ml heparin.

Also included in the present invention is a method of providing neurons to a subject affected by a condition characterized by the loss of neurons, which includes adhesively culturing stem cells and/or progeny thereof in vitro with a mixture including a mitogenic growth factor, a heparin-like agent, and an extracellular matrix component and implanting the treated cells into the spinal cord or brain of the subject, where they differentiate into neurons.

Also included in the present invention is a method of providing cholinergic neurons to a subject affected by a condition characterized by the loss of cholinergic neurons, which includes adhesively culturing stem cells and/or progeny thereof in vitro with a mixture including basic fibroblast growth factor, laminin and heparin, and implanting the treated cells into the spinal cord or brain of the subject, where they differentiate into cholinergic neurons. Typically, at least 50% of the neurons formed are cholinergic neurons. This method may, for example, be used in subjects affected with AD, ALS or a spinal cord injury Also included in the present invention a method of providing glutamatergic neurons to a subject affected by a condition characterized by the loss of glutamatergic neurons which includes adhesively culturing stem cells and/or progeny thereof in vitro with a mixture including basic fibroblast growth factor, laminin and heparin, and implanting the treated cells into the prefrontal cortex of the subject, where they differentiate into glutamatergic neurons. Typically, at least 50% of the neurons formed are glutamatergic neurons. This method may, for example, be used in subjects affected with head injury or stroke-related dementia.

Also included in the present invention is a method of providing GABAergic neurons to a subject affected by a condition characterized by the loss of GABAergic neurons, which includes adhesively culturing stem cells and/or progeny thereof in vitro with a mixture including basic fibroblast growth factor, laminin and heparin, and implanting the treated cells into the hippocampus of the subject, where they differentiate into GABAergic neurons. Typically, at least 50% of the neurons formed are GABAergic neurons. This method may, for example, be used in subjects affected with head injury or stroke-related dementia.

The present invention also includes a method of priming neuronal stem cells to differentiate into a specific neuronal phenotype, which includes adhesively culturing the neuronal stem cells in vitro with a mixture comprising a mitogenic growth factor, a heparin-like agent and an extracellular matrix component.

The invention further includes a method of priming neuronal stem cells to differentiate into a specific neuronal phenotype by adhesively culturing the neuronal stem cells in vitro with a mixture including basic fibroblast growth factor, laminin and heparin. The invention also includes a method of producing cells primed to become cholinergic neurons, glutamatergic neurons or GABAergic neurons by adhesively culturing stem cells and/or progeny thereof in vitro, for example, with a mixture of up to about 20 ng/ml basic fibroblast growth factor, about 0.5 µg/ml to about 5 µg/ml laminin, and about 0.5 µg/ml to about 10 µg/ml heparin.

The invention further includes a method of screening agents that effect the development of neurons by adhesively culturing stem cells and/or progeny thereof in vitro with a mixture including basic fibroblast growth factor, laminin and heparin, treating the cultured stem cells and/or progeny thereof with the agent, implanting the cultured stem cells and/or progeny into mammalian spinal cord or brain, and comparing the development of neurons in the implant derived from treated cells to the development of neurons in an implant derived from non-treated cells, wherein a difference in the development of neurons between the implants derived from treated versus non-treated cells indicates that the agent effects the development of neurons.

The present invention also includes a method of screening agents that effect the development of cholinergic neurons by adhesively culturing stem cells and/or progeny thereof in vitro with a mixture including basic fibroblast growth factor, laminin and heparin, treating the cultured stem cells and/or progeny thereof with the agent, implanting the cultured stem cells and/or progeny into a mammalian spinal cord or the medial septum region of a mammalian brain, and comparing the development of cholinergic neurons in the implant derived from treated cells to the development of cholinergic neurons in an implant derived from non-treated cells, wherein a difference in the development of cholinergic neurons between the implants derived from treated versus non-treated cells indicates that the agent effects the development of cholinergic neurons.

The present invention also includes a method of screening agents that effect the development of glutamatergic neurons by adhesively culturing stem cells and/or progeny thereof in vitro with a mixture including basic fibroblast growth factor, laminin, and heparin, treating the cultured stem cells and/or progeny thereof with the agent, implanting the cultured stem cells and/or progeny into a prefrontal cortex region of a mammalian brain, and comparing the development of glutamatergic neurons in the implant derived from treated cells to the development of glutamatergic neurons in an implant derived from non-treated cells, wherein a difference in the development of glutamatergic neurons between the implants derived from treated versus non-treated cells indicates that the agent effects the development of glutamatergic neurons.

The present invention also includes a method of screening agents that effect the development of GABAergic neurons by adhesively culturing stem cells and/or progeny thereof in vitro with a mixture including basic fibroblast growth factor, laminin, and heparin, treating the cultured stem cells and/or progeny thereof with the agent, implanting the cultured stem cells and/or progeny into the hippocampus region of a mammalian brain, and comparing the development of GABAergic neurons in the implant derived from treated cells to the development of GABAergic neurons in an implant derived from non-treated cells, wherein a difference in the development of GABAergic neurons between the implants derived from treated versus non-treated cells indicates that the agent effects the development of GABAergic neurons.

Also included in the invention is a method of screening agents that effect the development of neurons by adhesively culturing stem cells and/or progeny thereof in vitro with a mixture including basic fibroblast growth factor, laminin, and heparin; treating the cultured stem cells and/or progeny thereof with the agent; continuing to culture the stem cells and/or progeny thereof in vitro; and comparing the development of a neuronal phenotype in the treated stem cells and/or progeny to the development of a neuronal phenotype in non-treated stem cells and/or progeny thereof; where a difference in the development of a neuronal phenotype between the treated and non-treated cells indicates that the agent effects the development of neurons. The culture mixture may, for example, include up to about 20 ng/ml basic fibroblast growth factor, about 0.5 µg/ml to about 5 µg/ml laminin, and about 0.5 µg/ml to about 10 µg/ml heparin.

Further included in the present invention are stems cells and/or progeny thereof primed to become neurons by adhesively culturing in vitro with a mixture including a mitogenic growth factor, a heparin-like agent and an extracellular matrix component. The invention also includes stems cells and/or progeny thereof primed to become neurons by adhesively culturing in vitro with a mixture including basic fibroblast growth factor, laminin, and heparin, which may, for example be at a concentration of up to about 20 ng/ml basic fibroblast growth factor, about 0.5 µg/ml to about 5 µg/ml laminin, and about 0.5 µg/ml to about 10 µg/ml heparin.

BRIEF DESCRIPTION OF THE DRAWINGS

FIGS. 1a-1d are phase contrast images of FHL-primed (FIGS. 1a and 1c) or bFGF/laminin-treated cells (FIGS. 1b and 1d) for 1 day (FIGS. 1a and 1b) or for 6 days followed by a 10-day differentiation in B27 basic medium (FIGS. 1c and 1d). FIGS. 1e-1h show immunofluorescent staining on FHL-primed and differentiated hNSCs with specific antibodies. Antibody specificities are as follows; neuron specific type III b-tubulin (TUJ1) in FIG. 1e, immature and mature cholinergic neurons (Islet-1) in FIG. 1f, choline acetyltransferase (ChAT) in FIG. 1k and synapsin I (Syn) in FIG. 1h. FIG. 1i is a phase contrast image of typical cells used for electrophysiological recordings shown in FIGS. 1j-1k. An action potential evoked by a supra-threshold stimulus (FIG. 1j) was blocked by Tetrodotoxin treatment (FIG. 1k). Scale=40 µm.

FIG. 2a-2d are confocal images (merged from 30 1.2-µm confocal sections) of GFP-expressed hNSCs grafted in prefrontal cortex (FIG. 2a), medial septum (FIG. 2b), hippocampus (FIG. 2c), and spinal cord (FIG. 2d). FIG. 2e, GFP-green cells were double-labeled with the human specific nucleic marker, hN. FIG. 2f, GFP-green cells were not labeled with a polyclonal antibody specifically against rat cytochrome P450scc. FIG. 2g, hNSCs acquired a typical morphology of pyramidal neurons in the CA1 region of the hippocampus. FIG. 2h, the majority of hNSCs were double-labeled with a neuron specific marker, NeuN. 1-µm confocal sections from prefrontal cortex (CX, FIG. 2i-2k), dentate gyrus of hippocampus (DG, FIGS. 2l-2n), medial septum (MS, FIG. 2o-2q) and spinal cord (SC, FIG. 2r-2t) were immunofluorescent labeled with another neuron specific marker, TUJ1. Scale bars=100 µm. Asterisk (*), midlines.

FIG. 3a-3c are medial septum (MS); FIG. 3d-3i are spinal cord (SC); FIG. 3j-3l are cortex (CX); and FIG. 3m-3o are hippocampus (CA1). FIGS. 3b, 3e and 3h indicate immunostaining with specific antibodies against ChAT; FIG. 3k indicates immunostaining with a glutamate-specific antibody; and FIG. 3n indicates immunostaining with a GABA-specific antibody. FIG. 3a-3f and 3j-3o are 1 µm confocal images; FIG. 3g-3i are 0.3 µm confocal images. Scale=100 µm.

FIG. 4 shows the quantitative analyses of region-specific differentiation of neuronal subtypes from grafted hNSCs in adult rat CNS. The Y-axis represents the percentage of each neuronal phenotype over the total number of GFP-green cells. Cholinergic, glutamatergic and GABAergic neurons were identified by immunostaining with antibodies against ChAT, glutamate and GABA, respectively. Regions of the CNS studies are cortex (CX); medial septum (MS); CA1 of hippocampus (HIP); and spinal cord (SC). Error bars, ±s.e.m (n=0).

In FIG. 5d cells with clear neuronal morphology have spread to both sides of the ventral horn up to 8 mm from the injection site. FIGS. 5a, 5b and 5c indicates hNSCs-derived cholinergic neurons in adult rat spinal cord. Polyclonal anti-ChAT antibody was used at a 1:30 dilution. The secondary antibody conjugated with Alexa594 was used at a 1:200 dilution. Staining shown in FIG. 5a is natural fluorescent labeling of GFP. Staining shown in FIG. 5b is Alexa594 labeling for ChAT. In FIG. 5c, double-labeled cells are cholinergic neurons from hNSC origin.

DETAILED DESCRIPTION OF THE PREFERRED EMBODIMENTS

The present invention is directed to a simple yet efficient in vitro priming procedure that results in neural stem cells becoming neurons when grafted into non-neurogenic or neurogenic areas of the CNS. Furthermore, transplanted cells differentiate by acquiring cholinergic, glutamatergic and/or GABAergic phenotypes in a region-specific manner. For example, when transplanted into medial septum or spinal cord, they preferentially differentiate into cholinergic neurons; when transplanted into frontal cortex they preferentially differentiate into glutamatergic neurons; and when transplanted into hippocampus they preferentially differentiate into GABAergic neurons. Neurons "preferentially differentiate" into neurons of a specific phenotype when at least 50% of the neurons are of a specific phenotype. These neurons can be used to replace the neurons lost or damaged in neurodegenerative disease, including, but not limited to AD and ALS, or neurotrauma, including, but not limited to, spinal cord injury, head injury and stroke-related dementia.

The priming procedure of the present invention includes adhesively cultured neural progenitor cells, including neural stem cells and/or progeny thereof in vitro with a mixture of a mitogenic growth factor, a heparin-like agent, and an extracellular matrix component. Cells are "adhesively cultured" when they are cultured in conditions that promote the attachment of the cells to a fixed substrate. Methods for adhesively culturing cells are routine and well known. For example, to facilitate cell attachment, the culture substrate may be coated with agents such as poly-D-lysine, poly-L-ornithine, laminin or combinations thereof.

The culture medium contains at least one mitogenic growth factor. As used herein, the term "mitogenic growth factor" refers to a protein, peptide or other molecule having a growth, proliferative, differentiative, or trophic effect on neural stem cells and/or neural stem cell progeny. Growth factors which may be used for inducing proliferation include any trophic factor that allows neural stem cells and precursor cells to proliferate, including any molecule which binds to a receptor on the surface of the cell to exert a trophic, or growth-inducing effect on the cell. Such growth factors include, but are not limited to, basic fibroblast growth factor (bFGF), acidic fibroblast growth factor (aFGF), epidermal growth factor (EGF), leukemia inhibitory factor (LIF), neurotrophin-3 (NT-3), neurotrophin-4 (NT-4), brain-derived neurotrophic factor (BDNF), transforming growth factor alpha (TGFα), nerve growth factor (NGF), platelet-derived growth factor (PDGF), thyrotropin releasing hormone (TRH), transforming growth factor beta (TGFβ), insulin-like growth factor, and combinations thereof.

Growth factors are usually added to the culture medium at concentrations ranging between about 1 fg/ml to about 1 mg/ml. Concentrations between about 1 to about 100 ng/ml are usually sufficient. Simple titration experiments can be easily performed to determine the optimal concentration of a particular growth factor.

Basic FGF is one example of a mitogenic growth factor that can be added to the culture mixture. Preferably, it is present in the mixture at a concentration of at least about 10 ng/ml. Preferably, it is present in the mixture at a concentration of no more than about 50 ng/ml. More preferably, it is present in the mixture at a concentration of no more than about 20 ng/ml. Basic FGF is a member of the fibroblast growth factor family, which consists of at least nine distinct members (Basilico et al., *Adv. Cancer Res.* 59:115-165, 1992 and Fernig et al., *Prog. Growth Factor Res.* 5(4):353-377, 1994) which generally act as potent mitogens for a variety of cells of mesodermal, ectodermal and endodermal origin and have been shown to modulate the differentiation of neuronal cells. The genes for each has been cloned and sequenced. All the members of the FGF family bind heparin based on structural similarities. (Ornitz et al., *J. Biol. Chem.* 271(25):15292-15297, 1996).

Included in the mitogenic growth factors of the present invention are analog proteins which contain accidentally or deliberately induced alterations, such as deletions, additions, extensions, or exchanges of amino acid residues, so long as the biological activity of the growth factor, as measured by in vitro assay or immunological cross-reactivity assay, is retained. Analogs of bFGF are described in U.S. Pat. No. 6,294,359. In vitro assays used to assay for bFGF activity have been described by Gospodarowicz, et al, *J Cell Physiol* (1985) 122:323-332; Gospodarowicz, et al, *J Cell Biol* (1983) 97:1677-1685; Esch et al, *Proc Natl Acad Sci* (USA) (1985) 82:6507-6511; and Gospodarowicz, et al, *J Cell Physiol* (1986) 127: 121-136.

The culture medium of the present invention contains at least one heparin-like agent. As used herein, the term "heparin-like agent" includes, but is not limited to, heparin, heparan sulfate, heparin-like glycosaminoglycans, and heparan-like glycosaminoglycans. These heparin-like agents are members of a class known as glycosaminoglycans (GAG) and are known to inhibit smooth muscle cell proliferation. Hexasaccharides-decasaccharides obtained from partial nitrous acid digestion of heparin bind to acidic fibroblast growth factor and aid its mitogenic activity in fibroblasts, but inhibit the proliferation of endothelial cells under some conditions (Barzu, T., et al., *J Cell Physiol* (1989) 140:538-548).

Heparin is one example of a heparin-like agent that can be added to the culture mixture of the present invention. Preferably the heparin is present in the mixture at a concentration of at least about 0.5 μg/ml. Preferably the heparin is present in the mixture at a concentration of no more than about 10 μg/ml. More preferably the heparin is present in the mixture at a concentration of no more than about 5 μg/ml.

The culture medium of the present invention contains at least one extracellular matrix component. As used herein, the term "extracellular matrix component" includes, but is not limited to, laminin, fibronectin, collagen, MATRIGEL™ and combinations thereof. Laminin is one example of an extracellular matrix component that can be added to the culture mixture of the present invention. Preferably, the laminin is present in the mixture at a concentration of at least about 0.5 μg/ml. Preferably, the laminin is present in the mixture at a concentration of no more than about 5 μg/ml laminin. More preferably, the laminin is present in the mixture at a concentration of no more than about 1 μg/ml.

Optionally, the culture medium of the present invention can also include the mammalian Sonic Hedgehog protein or an N-terminus-containing fragment thereof. Preferably, the Sonic Hedgehog protein or an N-terminus-containing fragment thereof is present in the mixture at a concentration of at least about 0.05 μg/ml. Preferably, the Sonic Hedgehog protein or an N-terminus-containing fragment thereof is present in the mixture at a concentration of no more than about 1.0 μg/ml. More preferably, the Sonic Hedgehog protein or an N-terminus-containing fragment thereof is present in the mixture at a concentration of at least about 0.5 μg/ml. Additionally, the mixture may contain other tropic factors or chemicals important in the development of cholinergic neurons (Jessell, Nat. Rev. Genet. 1, 20-29 (2000) and Anderson, Neuron 30, 19-35 (2001)) including, but not limited to all trans-retinoic acid, nerve growth factor (NGF), brain-derived neurotrophic factor (BDNF), neurotrophin-3 (NT-3) and neurotrophin-4 (NT-4).

Cholinergic, glutamatergic and GABAergic neurons are identified by immunostaining with antibodies against ChAT, glutamate and GABA, respectively.

The stem cells and/or progeny thereof are adhesively cultured in vitro in a treatment mixture of the present invention for a time sufficient to see a change in the morphology (e.g., a spreading out and enlargement) of the cells. Typically, this change starts at about 24 hours after cell plating. The stem cells and/or progeny are preferably plated as spheres (but not dissociated cells) onto 0.01% poly-D-lysine and 0.5 μg/ml laminin coated culture dishes or glass coverslips. The basic medium is preferably DMEM/F-12 (1:1-3:1) plus 10 mM HEPES and 0.15% glucose.

For evaluation purposes, the cells can be labeled as described in the example below. These treated (i.e., primed) cells are implanted into a mammalian spinal cord or brain, wherein they differentiate into neurons. Cholinergic, glutamatergic and GABAergic neurons are identified by immunostaining with antibodies against ChAT, glutamate and GABA, respectively. These cells can be detected as early as one week, but more matured ChAT neurons are visible 1 month post transplantation. Although the examples below demonstrate the effect of implanting cells into a normal adult brain and spinal cord, it is believed that the primed (i.e., treated) cells will give rise to even more neurons in a degenerated brain or spinal cord because it is known that a degenerated brain or spinal cord provides more signals that may enhance the regional-specific neuronal differentiation.

Generally, the term "neural stem cell" is used to describe cells that: (i) can generate neural tissue or are derived from the nervous system; (ii) have capacity for self-renewal; and (iii) can give rise to cells other than themselves through asymmetric cell division. An important identifying feature of a stem cell is its ability to exhibit self-renewal or to generate more of itself. The simplest definition of a stem cell is a cell with the capacity for self-maintenance. A more stringent (but still simplistic) definition of a stem cell is provided by Potten and Loeffler (*Development* 1990; 110:1001) who have defined stem cells as "undifferentiated cells capable of a) proliferation, b) self-maintenance, c) the production of a large number of differentiated functional progeny, d) regenerating the tissue after injury, and e) a flexibility in the use of these options." The role of stem cells is to replace cells that are lost by natural cell death, injury, or disease. The presence of stem cells in a particular type of tissue usually correlates with tissues that have a high turnover of cells. However, this correlation may not always hold, as stem cells are thought to be present in tissues (e.g., liver) that do not have a high turnover of cells.

As used herein, a stem cell is capable of self-maintenance, meaning that with each cell division, one daughter cell will also be a stem cell. The non-stem cell progeny of a stem cell are termed progenitor cells. The progenitor cells generated from a single multipotent neural stem cell are capable of differentiating into neurons, astrocytes (type I and type II) and oligodendrocytes. Some progenitor cells can produce progeny that are capable of differentiating into more than one cell type. For example, an O-2A cell is a glial progenitor cell that gives rise to oligodendrocytes and type II astrocytes, and thus could be termed a "bipotential" progenitor cell. A distinguishing feature of a progenitor cell is that, unlike a stem cell, it has limited proliferative ability and thus does not exhibit self-maintenance.

Stem cells from neural and other tissues are often defined by their tissue of origin. Human heterologous neural stem cells may be derived from fetal tissue following elective abortion, or from a post-natal, juvenile or adult organ donor. Autologous neural tissue can be obtained by biopsy, or from patients undergoing neurosurgery in which neural tissue is removed, for example, during epilepsy surgery, temporal lobectomies and hippocampalectomies. Neural stem cells have been isolated from a variety of adult CNS ventricular regions, including the frontal lobe, conus medullaris, thoracic spinal cord, brain stem, and hypothalamus, and proliferated in vitro using the methods detailed herein. In each of these cases, the neural stem cell exhibits self-maintenance and generates a large number of progeny which include neurons, astrocytes and oligodendrocytes.

Alternatively, stem cells can be defined by their potentiality (Gage, *Science*, 287, 1433-1438 (2000)). Understanding the potentiality of a cell is best described in the context of normal human development. As described in Stem Cells: A Primer, National Institutes of Health, May 2000 (found on the internet at nih.gov/news/stemcell/primer.htm), human development begins when a sperm fertilizes an egg and creates a single cell that has the potential to form an entire organism. This fertilized egg is totipotent, meaning that its potential is total. In the first hours after fertilization, this cell divides into identical "totipotent" cells. This means that either one of these cells, if placed into a woman's uterus, has the potential to develop into a fetus. In fact, identical twins develop when two totipotent cells separate and develop into two individual, genetically identical human beings. Approximately four days after fertilization and after several cycles of cell division, these totipotent cells begin to specialize, forming a hollow sphere of cells, called a blastocyst. The blastocyst has an outer layer of cells and inside the hollow sphere, there is a cluster of cells called the inner cell mass.

The outer layer of cells will go on to form the placenta and other supporting tissues needed for fetal development in the uterus. The inner cell mass cells will go on to form virtually all of the tissues of the human body. Although the inner cell mass cells can form virtually every type of cell found in the human body, they cannot form an organism because they are unable to give rise to the placenta and supporting tissues necessary for development in the human uterus. These inner cell mass cells are "pluripotent." This means that they can give rise to many types of cells but not all types of cells necessary for fetal development. Because their potential is not total, they are not totipotent and they are not embryos. Thus, if an inner cell mass cell were placed into a woman's uterus, it would not develop into a fetus (Stem Cells: A Primer, National Institutes of Health, May 2000).

The pluripotent stem cells undergo further specialization into stem cells that are committed to give rise to cells that have a particular function. Examples of this include blood stem cells that give rise to red blood cells, white blood cells and platelets; and skin stem cells that give rise to the various types of skin cells. These more specialized stem cells are called "multipotent" (Stem Cells: A Primer, National Institutes of Health, May 2000).

Most stem cells fall into the category of multipotent stem cells. Multipotent stem cells can be obtained from embryonic, post-natal, juvenile, or adult tissue. The tissue can be obtained from a wide variety of animals, such as insects, fish, reptiles, birds, amphibians, mammals, and the like. The preferred source is from mammals, preferably rodents and primates, and most preferably, humans. In the case of a heterologous donor animal, the animal may be euthanized, and the tissue (e.g., neural tissue) and specific area of interest removed using a sterile procedure. Areas of particular interest, for example, include any area from which neural stem cells can be obtained (e.g., any part of the nervous system, bone marrow, etc.).

Stem cells can be obtained from donor tissue by dissociation of individual cells from the connecting extracellular matrix of the tissue. Tissue from a particular region is removed using a sterile procedure, and the cells are dissociated using any method known in the art including treatment with enzymes such as trypsin, collagenase and the like, or by using physical methods of dissociation such as with a blunt instrument.

The stem cells can be cultured in suspension or on a fixed substrate. However, substrates tend to induce differentiation of the stem cell progeny. Thus, suspension cultures are preferred if large numbers of undifferentiated stem cell progeny are desired. Suitable culture media capable of supporting cell growth include HEM, DMEM, RPMI, F-12, and the like, which can contain supplements required for cellular metabolism such as glutamine and other amino acids, vitamins, minerals and useful proteins such as transferrin, and the like. The culture medium may also contain antibiotics to prevent contamination with yeast, bacteria, and fungi, such as penicillin, streptomycin, gentamicin, and the like. Conditions for culturing should be close to physiological conditions (preferably, a pH of about 6 to about 8, and a temperature of about 30° C. to about 40° C.). Stem cell progeny can be cryopreserved until they are needed by any method known in the art. The cells can be suspended in an isotonic solution, preferably a cell culture medium, containing a particular cryopreservant. Such cryopreservants include dimethyl sulfoxide (DMSO), glycerol, and the like.

The source of the stem cells and/or progeny thereof can be embryonic, fetal or adult neural and non-neural tissue (e.g., bone marrow or fat tissue). Preferably, they are multipotent fetal or adult stem cells (such as neural stem cells or hematopoietic stem cells) or pluripotent embryonic stem cells (such as those from inner mass cells of blastocyst). Methods for the isolation and in vitro culture of multipotent neural stem cells are reported, for example, by Armstrong and Svendsen (*Cell Transplant* 2000; 9:13952) and in U.S. Pat. No. 6,399,369.

Human neural stem cells (hNSCs) isolated from the cortex of an 8-wk human embryo (Svendsen et al., *J. Neurosci Methods* 1998; 85:141-52) have been expanded continuously for more than 101 weeks (80 passages) without any sign of slowing down. The population doubling time is around 4 days under optimal conditions. The expanded stem cells can be primed and directly implanted to a patient.

The instant invention allows the use of stem cells and/or progeny thereof that have been prepared from donor tissue that is xenogeneic and/or allogeneic to the host. In general, however, in order for allograft or xenografts to be successful it is preferred that some method of reducing or eliminating the immune response to the implanted tissue be employed. Thus, recipients will often be immunosuppressed, either through the use of immunosuppressive drugs such as cyclosporin, or through local immunosuppression strategies employing locally applied immunosuppressants.

As an alternative to employing immunosuppression techniques, methods of gene replacement or knockout using homologous recombination in embryonic stem cells (as taught by Smithies et al. *Nature* 1985; 317:230-234), and extended to gene replacement or knockout in cell lines (H. Zheng et al. *PNAS,* 1991; 88:8067-8071), can be applied to stem cells for the ablation of major histocompatibility complex (MHC) genes. Stem cells lacking MHC expression would allow for the grafting of enriched neural cell populations across allogeneic, and perhaps even xenogeneic, histocompatibility barriers without the need to immunosuppress the recipient.

The treated stem cells and/or progeny thereof can be administered to a host in a wide variety of ways. Cells can be administered to the desired region using any method that maintains the integrity of surrounding areas, preferably by local injection. Cells can also be administered to the systemic or portal circulation system.

In addition to stem cells or progeny thereof, pharmaceutical compositions useful for the methods of the present invention can include immunosuppressants, anti-inflammatory agents, etc. Additionally, if desired, stem cells or progeny thereof can be encapsulated, as is well known to one of skill in the art.

Survival of the graft in the living host can be examined using various methods including clinical, radiological, histological, physiological, etc. Non-invasive scans can be used, including computerized axial tomography (CAT scan or CT scan), nuclear magnetic resonance or magnetic resonance imaging (NMR or MRI), or positron emission tomography (PET) scans. Post-mortem examination of graft survival can be done by removing tissue, and examining the affected region macroscopically, or more preferably using microscopy. Cells can be stained with any stains visible under light or electron microscopic conditions, and more particularly with stains that are specific for neurons and glia. Monoclonal antibodies that identify neuronal cell markers, such as the Tuj 1 antibody (Sigma) and the NeuN antibody (Chemicon), are used to identify neurons. Monoclonal antibodies for human nuclei (Chemicon) are particularly useful to identify grafted cells with human origin. Most preferable are antibodies that identify neurotransmitters, particularly those directed to GABA, TH, and substance P, and to enzymes involved in the synthesis of neurotransmitters, in particular, ChAT or GAD. Transplanted cells can also be identified by prior incorporation of tracer dyes such as rhodamineor fluorescein-labeled microspheres, fast blue, bisbenzamide or genetically introduced histochemical markers such as the lac Z gene, which produces beta galactosidase, or natural fluorescent markers such as green fluorescent protein.

The methods of the present invention can be used for drug screening and/or biological studies in vitro and in vivo, to identify the effect of agents on neural cells and neuronal development. The term "agent" refers to any virus, protein, peptide, amino acid, lipid, carbohydrate, nucleic acid, nucleotide, drug, pro-drug or other substance that may have an effect on neural cells whether such effect is harmful, beneficial, or otherwise. The term encompasses any biologically or pharmaceutically active substance that may prove potentially useful for the proliferation, differentiation or functioning of CNS cells or treatment of neurological disease or disorder. For example, the term may encompass certain neurotransmitters, neurotransmitter receptors, growth factors, growth factor receptors, and the like, as well as enzymes used in the synthesis of these agents.

EXAMPLES

The present invention is illustrated by the following examples. It is to be understood that the particular examples, materials, amounts, and procedures are to be interpreted broadly in accordance with the scope and spirit of the invention as set forth herein.

Cell Culture of Human Neural Stem Cells (hNSCs).

Human neural stem cells (hNSCs), as described in Wu et al. *Gene Therapy* 2002; 9: 245-255, were obtained from Dr. Clive N. Svendsen, University of Wisconsin. The hNSCs were originally derived from the cortex of an 8-wk human postmortem embryo according to the guidelines of the Department of Health in the United Kingdom. After 15-wk in vitro culturing in Dr. Svendsen's laboratory, cells were shipped in cryovials.

The cell line was cultured in a T75 flask with 12 ml of serum-free DMEM:F12 (3:1, Life Technologies) supplemented with 20 ng/ml EGF (R & D Systems), 10 ng/ml bFGF (R & D Systems), 2.5 µg/ml heparin (Sigma), 10 ng/ml LIF (Chemicon), N2 (Bottenstein and Sato, *PNAS* 1979; 76:514-517), 15 mM HEPES (Sigma), 1.5% glucose (Sigma), 2 mM L-glutamine (Sigma) and 1× penicillin/streptomycin (Sigma). Cells were incubated with 8.5% $CO_2$ at 37° C. A half volume of medium was changed with fresh medium once every 34 days. Expanded neurospheres were dissociated into single cells once every 810 days, spheres were treated by 0.025% Trypsin (Sigma) and 200 U/ml DNase (Sigma) in calcium-free and magnesium-free PBS (Sigma) at 37° C. for 20 min. The Trypsin reaction was stopped by equal volume of the growth medium containing 1.2 mg/ml Trypsin inhibitor (Sigma). Spheres were then dissociated by trituration using silicon-coated fire-polished Pasteur pipette. Cells were seeded at $3-6 \times 10^6$ per T75 flask. For cryo-preservation, dissociated hNSCs were resuspended at $5-8 \times 10^6$ per milliliter of DMEM with 20% fetal bovine serum (FBS) (Life Technology) and 10% DMSO (Sigma), cooled slowly in a cry-container with isopropanol, stored first in a −80° C. freezer and then in liquid nitrogen. Recovery of hNSCs was performed by a quick thawing, rinsing with DMEM 2-3 times, and then culturing in the growth medium.

The basic priming procedure included an FHL treatment of adhesively cultured neurospheres for 5-7 days. The optimal conditions for FHL were 20 ng/ml bFGF, 5 µg/ml heparin and 1 µg/ml laminin (Invitrogen). In some of experiments, N-terminal recombinant mouse Sonic Hedgehog protein (Shh-N) (180 amino acids, Catalog No. 461, R & D Systems, Minneapolis, Minn.) was also added at concentrations ranging from 0.002 to 1 µg/ml, preferably at a concentration ranging from 0.05-0.5 µg/ml) (SFHL cocktail). For differentiation studies in vitro, small spheres (4-5 days post-passage) were seeded at $6-7 \times 10^4$ cells/cm$^2$ on glass coverslips pre-coated with 0.01% poly-D-lysine (Sigma) and 0.5 µg/cm$^2$ laminin (Invitrogen). After 5-7 days of priming in DMEM/F12 containing N2 and FHL, cells were switched to DMEM:F12 containing B27 (Life Technologies) alone or with other neurotrophic factors for an additional 7 to 14 days.

For transplantation, neurospheres from passages 19 to 55 were plated in T25 culture flasks pre-coated with 0.01% poly-D-lysine (Sigma). Cells were primed with FHL or SFHL for a total of 6-7 days, and treated with the CAGegfp rAAV vector at an MOI of 2-5 (transducing particles/cell) for 3-4 days before grafting, as described in Wu et al. *Gene Therapy* 2002; 9:245-255. The CAGegfp viral stock was prepared and titrated as previously described. (Wu et al. *Gene Therapy* 2002; 9:245-255). The CAGegfp rAAV vector is an adeno-associated viral (AAV) vector containing enhanced green fluorescent protein (GFP). Recombinant AAV can transfer genes into both dividing and non-dividing cells (such as neurons) without cytotoxicity. GFP is a marker that allows for the identification of transplanted cells very easily through a direct examination under a fluorescent microscope. Just before transplantation, cells were trypsinized and dissociated as described above. A single cell suspension was obtained at $1-5 \times 10^4$ cells/ml in DMEM plus 200 U/ml DNase.

Electrophysiological Recording.

Resting and action potentials of cells were recorded at room temperature (20-23° C.) using an Axopatch-200A patch clamp amplifier (Axon Instruments, Foster City, Calif.). Cells were kept on glass coverslips in the basic differentiation medium for 7 to 14 days after FHL or SFHL priming, and then transferred to a recording chamber with the medium containing 140 mM NaCl, 4 mM KCl, 10 mM HEPES, 10 mM glucose, 2 mM CaCl$_2$ and 1 mM MgCl$_2$ (pH=7.4). The pipette solution contained 120 mM KMeSO$_3$, 20 mM KCl, 1 mM CaCl$_2$, 1 mM BAPTA, 10 mM HEPES and 2 mM Mg-ATP (pH=7.2). The recorded signals were filtered at 2 kHz, sampled at 200 µs per point and analyzed with the IGOR programs (WaveMetrics, Lake Oswego, Oreg.).

Immunocytochemistry.

Cells for in vitro study were fixed with 4% paraformaldehyde (PFA). Animals were perfused with 4% PFA 1 week to 1 month post-grafting, cryosectioned coronally for brain and longitudinally for spinal cord at 48 µm. Cells or sections were subjected to immunofluorescent staining as described in Wu et al. *Gene Therapy* 2002; 9:245, using mouse anti-Class III b-tubulin (TUJ1) (1:4,000, Covance BAbCo), mouse anti-Islet I (1:50, Developmental Studies Hybridoma Bank), goat anti-ChAT (1:100, Chemicon), rabbit anti-synapsin 1 (1:500, Chemicon), mouse anti-NeuN (1:100, Chemicon), mouse anti-human nuclei (1:100, Chemicon), rabbit anti-GABA (1:1,000, Sigma), rabbit anti-glutamate (1:5,000, Sigma), rabbit anti-GFAP (1:1,000, Chemicon), rabbit anti-TH (1:500, Chemicon), mouse anti-human Nestin (1:200, C. A. Messam, NIH) (Messam et al. *Exp. Neurol.* 2000; 161:585-596) or mouse anti-GalC (1:100, Chemicon). The Alexa Fluo 594-conjugated secondary antibodies, goat anti-mouse, goat anti-rabbit or donkey anti-goat (all from Molecular Probe), were used at 1:200. Cell nuclei were counterstained with 1 µg/ml DAPI (Sigma).

Sections or cells were incubated for 30 minutes in 5% normal serum+5% bovine serum albumin with 0.1% Triton X-100. The block of nonspecific binding and permeablization were followed with a brief rinse in PBS. Sections or cells were incubated for 4 hours at 4° C. with the primary antibody against ChAT (Chemicon) at a 1:50-1:60 dilution, and then rinsed with PBS 3 times at 15 minutes each. This was followed by incubation with Alexa fluorophore-conjugated secondary IgG (Molecular Probes), 594 donkey anti-goat at an optimal concentration of 1:100 for 1 hour at room temperature in the dark. After three 15-minute rinses with PBS, whole spinal cord sections were mounted with Fluoromount G (Fisher), some tissue sections were subjected to counterstaining with 1 µg/ml DAPI (Sigma) at room temperature for 5 minutes, followed by a brief rinse in PBS and then mounted. All the labeled sections were examined under a fluorescent or a confocal microscope.

Quantification.

Cell profiles were counted using an Olympus Fluoview confocal microscope (Leeds Instruments) with a 20× objective. Nine or three semi-serial sections at least 240 µm apart were immunostained with ChAT or other antibodies (TUJ1, NeuN, GABA, glutamate), respectively. The number of green GFP-labeled cells (representing grafted hNSCs) and the number of double-labeled cells (for each phenotype) were counted in three randomly chosen confocal sections (1 µm thickness) and averaged for each cryostat section (48 µm). Moreover, averaged percentages of double-labeled cell profiles over nine or three cryostat sections per rat were further averaged from 5 animals for each cell phenotype in each grafted areas of the CNS. Repeated measures ANOVA were performed for statistical analyses using the InStat program (GraphPad Software, Inc.).

In Vitro Priming and Differentiation.

To obtain cholinergic neurons, multipotent hNSCs were treated with trophic factors or other chemicals important in the development of cholinergic neurons. The agents included recombinant human basic fibroblast growth factor (bFGF), epidermal growth factor (EGF), leukemia inhibitory factor (LIF), mouse sonic hedgehog-amino-terminal peptide (Shh-N), all trans-retinoic acid, nerve growth factor (NGF), brain-derived neurotrophic factor (BDNF), neurotrophin-3 (NT-3), neurotrophin-4 (NT-4), natural mouse laminin and heparin. Long-term epigenetically expanded hNSC spheres (19-55 passages) were plated onto poly-D-lysine and laminin-coated dishes and treated with the above agents in vitro at various concentrations either alone or in combination, concurrently or sequentially.

Figure 1:
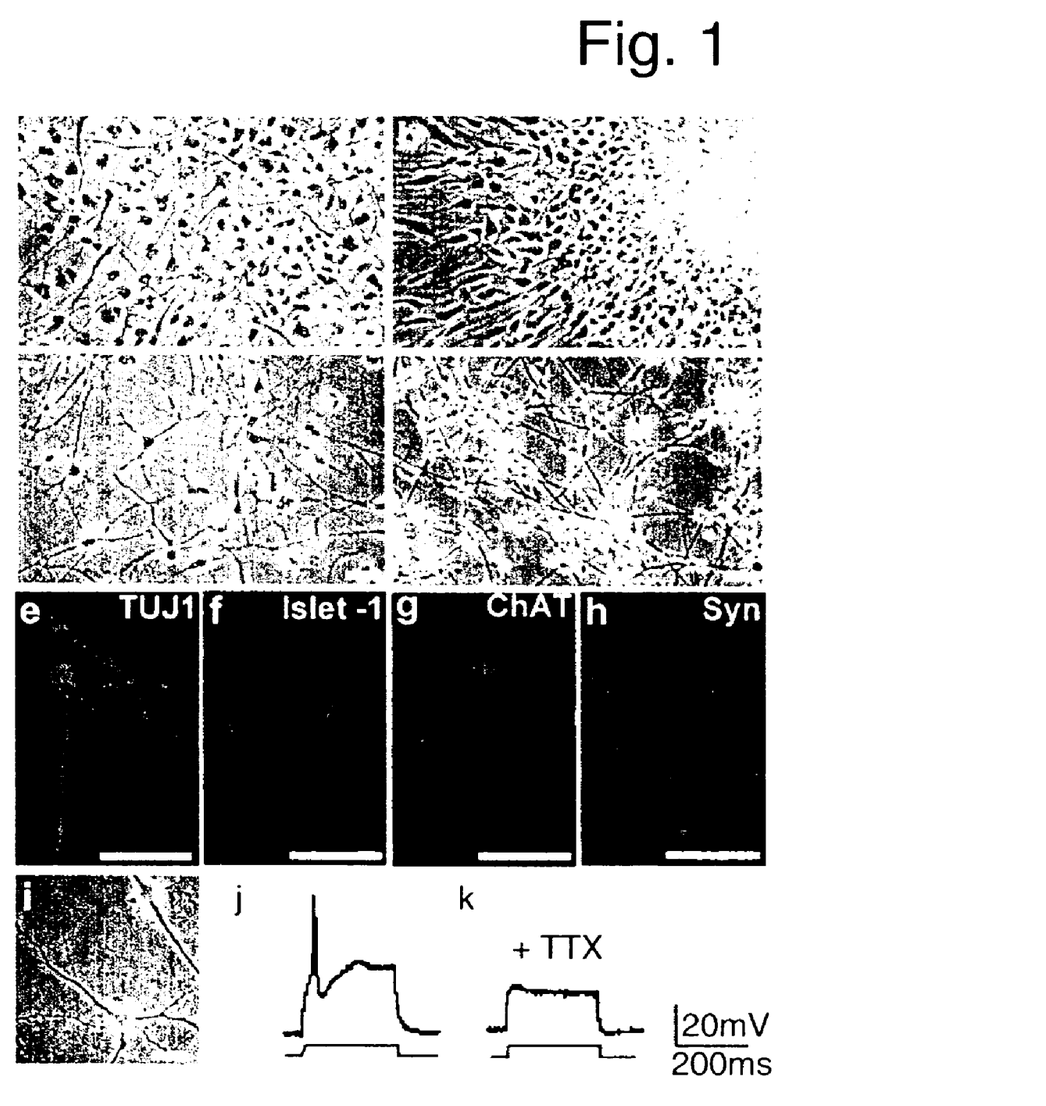
FIG. 1 shows morphological, immunocytochemical and electrophysiological characterization of primed and differentiated hNSCs in vitro.

A one-day exposure to the combination of bFGF, heparin and laminin (abbreviated as FHL), with or without Shh-N (the combination of Shh-N and FHL is abbreviated as SFHL), resulted in a rapid spreading of large planar cells in culture (FIG. 1a). In contrast, treatment with other combinations of bFGF, heparin, laminin and Shh-N [such as bFGF plus laminin (FL)] for one day gave rise to limited radial spread of spindle-shaped cells, with the cells remaining close to the cores of the spheres (FIG. 1b), similar to that described in Svendsen et al. *J. Neurosci. Methods* 1998; 85:141-152. Likewise, a rapid spreading of large planar cells in culture was not observed with combinations containing EGF, LIF, NT-3 or NT-4.

Following a 6-day priming and a 10-day further differentiation in basic medium containing B27, large multipolar neuronal-like cells were often found near the edge of the FHL-primed spheres (FIG. 1c), while most of the neuronal-like cells were small and bipolar in other treatment groups (FIG. 1d).

Immunocytochemical analyses indicated that the small bipolar cells (<20 μm) were either GABAergic or glutamatergic (data not shown), similar to what has been described previously in Caldwell et al. *Nat. Biotechnol.* 2001; 19:475-479.

On the other hand, many of the large multipolar cells near the edge of FHL-primed spheres, whose neuronal phenotype was shown by immunocytochemical staining using a monoclonal antibody against the neuron specific type III b-tubulin, TUJ1 (FIG. 1e), were cholinergic because they showed immunoreactivity to markers specific for immature and mature cholinergic neurons, Islet-1 (FIG. 1f) and choline acetyltransferase (ChAT, FIG. 1g), respectively. Some of these neurons also expressed synapsin I (FIG. 1h). No ChAT or Islet-1 positive cells were detected in hNSCs with other treatments. These ChAT+ neurons accounted for about 20-70% of cell populations near the monolayer edge of spheres. However, multiple layers in and around the core of spheres prevented accurate quantification of percentage of ChAT+ cells in total populations. Furthermore, ChAT+ neurons became undetectable if differentiated cells were subjected to further dissociation and re-plating, a procedure described previously in Caldwell et al. *Nat. Biotechnol.* 2001; 19:475-479. In addition to the cholinergic neurons, significant numbers of small bipolar neurons and astrocytes were also detected in FHL-primed neurospheres even after a prolonged in vitro differentiation.

To determine whether these cells have the electrical characteristics of neurons, resting potentials and action potentials were monitored using the whole-cell patch clamp recording technique. Seven days after FHL-primed treatment, most of the large multipolar cells had resting potentials (−29.0±2.0 mV, n=6), but no action potentials could be evoked. These resting potentials became much more negative (−63.6±3.0 mV, n=5) 14 days after FHL treatment, and action potentials were seen when depolarizing currents were injected (FIG. 1j). The action potentials were blocked by 1 mM tetrodotoxin (FIG. 1k). Thus, the FHL-priming procedure directs some of hNSCs in vitro to become functional neurons.

In this example, the priming cocktail contained 20-ng/ml bFGF, 5 μg/ml heparin and 1 μg/ml laminin. Initial screening indicated that both bFGF and heparin were necessary to obtain large cholinergic neurons from hNSCs in vitro. An adherent laminin substrate pre-coated on the culture dishes and included in the priming media was also required for an optimal spreading of neurospheres, which presumably function by allowing cells inside the spheres to be exposed evenly to the bFGF/heparin treatment. Using this priming method, a significant number of large multipolar cholinergic neurons differentiate from hNSCs following further incubation in the B27 medium without bFGF. In contrast, direct plating of mitogen-expanded hNSCs onto laminin-coated culture dishes generated only small bipolar GABAergic and glutamatergic neurons, even when cells were treated with various neurotrophic factors (Caldwell et al., *Nat. Biotechnol.* 2001; 19:475-479). Similar effects were observed on hNSC differentiation in vitro when cells were treated with all trans-retinoic acid, EGF, LIF, ShhN and heparin, alone or in combination.

Neuronal Differentiation of Grafted hNSCs in Adult Rat CNS.

To demonstrate that hNSCs primed by FHL- or SFHL for 6-7 days in vitro become neurons in vivo, primed cells from the same batch were injected into a neurogenic region (the hippocampus) and several non-neurogenic regions in adult rats. Non-neurogenic regions including prefrontal cortex and medial septum. To trace the grafted cells, primed hNSCs were transduced with a recombinant adeno-associated viral (rAAV) vector containing an enhanced green fluorescent protein (GFP). This method was chosen because GFP labels both cell bodies and processes without leakage, (Schmitz and Bereiter-Hahn, *Histochemistry & Cell Biology* 2001; 116:89-94) and can be directly visualized without further staining procedures. About 80% of cells become GFP+ without apparent cytotoxicity. Furthermore, GFP+ hNSCs maintain a similar neuronal and glial differentiation profile to untransduced hNSCs. See Wu et al. *Gene Therapy* 2002; 9:245-255.

Single cell suspension of hNSCs were kept on ice until transplantation and pipetted once every hour. All procedures followed the NIH guidelines for the care and use of laboratory animals. Male Sprague-Dawley rats (Harlan), 240-270 g, were grafted with primed and AAV-labeled hNSCs either into brain (n=12) or spinal cord (n=10). Animals were immunosuppressed with NEORAL cyclosporine (Novartis Pharma AG, East Hanover, N.J.) at 100 μg/ml in drinking water 3 days before surgery and thereafter. 50,000 dissociated cells in 2 μl were stereotaxically injected into prefrontal cortex (AP: +2.7 mm; ML: −0.8 mm; DV: −3.0 mm from skull), medial septum (AP: +0.7 mm; ML: +0.2 mm; DV: −7.0 mm), or hippocampus (AP: −4.3 mm; ML: +2.5 mm; DV: −3.0 mm). 50,000 hNSCs were transplantation in the spinal cord (ML: +1 mm; DV: −1.5 mm from dura). AP, anteroposterior axis; ML, mediolateral axis; DV, dorsoventral axis.

Figure 2:
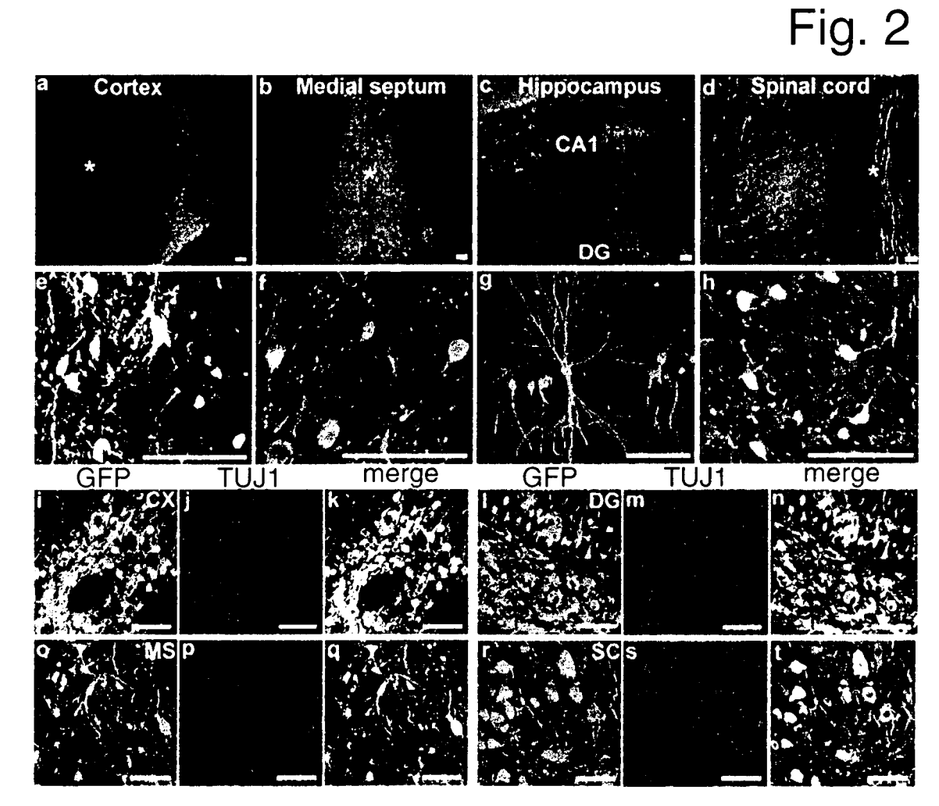
FIG. 2 shows neuronal differentiation and integration of primed hNSCs one month post-grafting in various regions of brain and spinal cord of adult rats.

One to two weeks after grafting approximately $5 \times 10^4$ primed and labeled hNSCs into either rat brain or spinal cord, GFP+ cells survived and were found mainly near the injection sites (data not shown). Apparent migration and integration could be seen one month post-transplantation (FIGS. 2a-d). The extent of migration was variable depending on the regions injected. In prefrontal cortex, for example, GFP+ cells were usually located within 0.4-2 mm of the injection site. However, cells migrate much farther, up to 1-2 cm, when grafted into medial septum, hippocampus or spinal cord. More interestingly, the distribution of transplanted cell bodies and processes followed endogenous patterns in the highly organized CNS regions, including cortex (FIG. 2a), medial septum (FIG. 2b), hippocampus (FIG. 2c), and spinal cord (FIG. 2d). Green neuronal fibers were detectable as early as 1 week after transplantation, and much more abundant in 1 month grafts. This is in contrast to a previous study using undifferentiated cells, which observed neuronal fibers mainly in 20-week grafts. See Ostenfeld et al., *Exp. Neurol,* 2000; 164:215-226. To exclude the possibility of host cells picking up leaked GFP DNA or proteins from damaged hNSCs, control transplantations were performed using freeze-thawed hNSCs, which were pre-treated with the same priming procedure and rAAV-transduction as the experimental groups. No green fluorescent cells were detected in the host tissue in these control rats at least ten days after surgery (data not shown). In animals transplanted with live hNSCs, all nucleated GFP+ cells originated from the grafted hNSCs as verified by positive labeling with a monoclonal antibody specifically against human nuclei (FIG. 2e), and negative labeling with a specific antibody for rat cytochrome P450 side chain cleavage enzyme (P450scc, FIG. 2f). Therefore, the data indicated that these green fluorescent cells were indeed derived from the human origin, but not from the host cells either by leaking of GFP from damaged hNSCs or spontaneous fusion between human and rat cells. See Ying et al., *Nature* 2002; 416:545-548 and Terada et al., *Nature* 2002; 416:542-545. Further morphological examination of the hNSCs grafts showed that GFP+ cells in the pyramidal cell layer of the CA1 region of the hippocampus acquired typical pyramidal cell characteristics (FIG. 2g). The numerous spines on their processes indicated a functional maturation of these grafted hNSCs. Immunocytochemical analyses using neuron specific markers, NeuN (FIG. 2h) and TUJ1 (FIGS. 2i-t), revealed that most GFP+ cells acquire neuronal labeling 1 month after transplantation into cortex (FIGS. 2i-k), hippocampus (FIGS. 2l-n), medial septum (FIGS. 2o-q) or spinal cord (FIG. 2r-t). Only a few scattered GFP+cells were double labeled with an astrocyte-specific marker, glial fibrillary acidic protein (GFAP) (data not shown). No green cells were immunoreactive to a monoclonal antibody against galactocerebroside (GalC, data not shown), indicating the absence of oligodendrocyte differentiation from grafted hNSCs. In addition, negative staining using an undifferentiated neural stem cell marker, nestin (data not shown), suggested that all grafted cells had differentiated by one month after transplantation.

Figure 3:
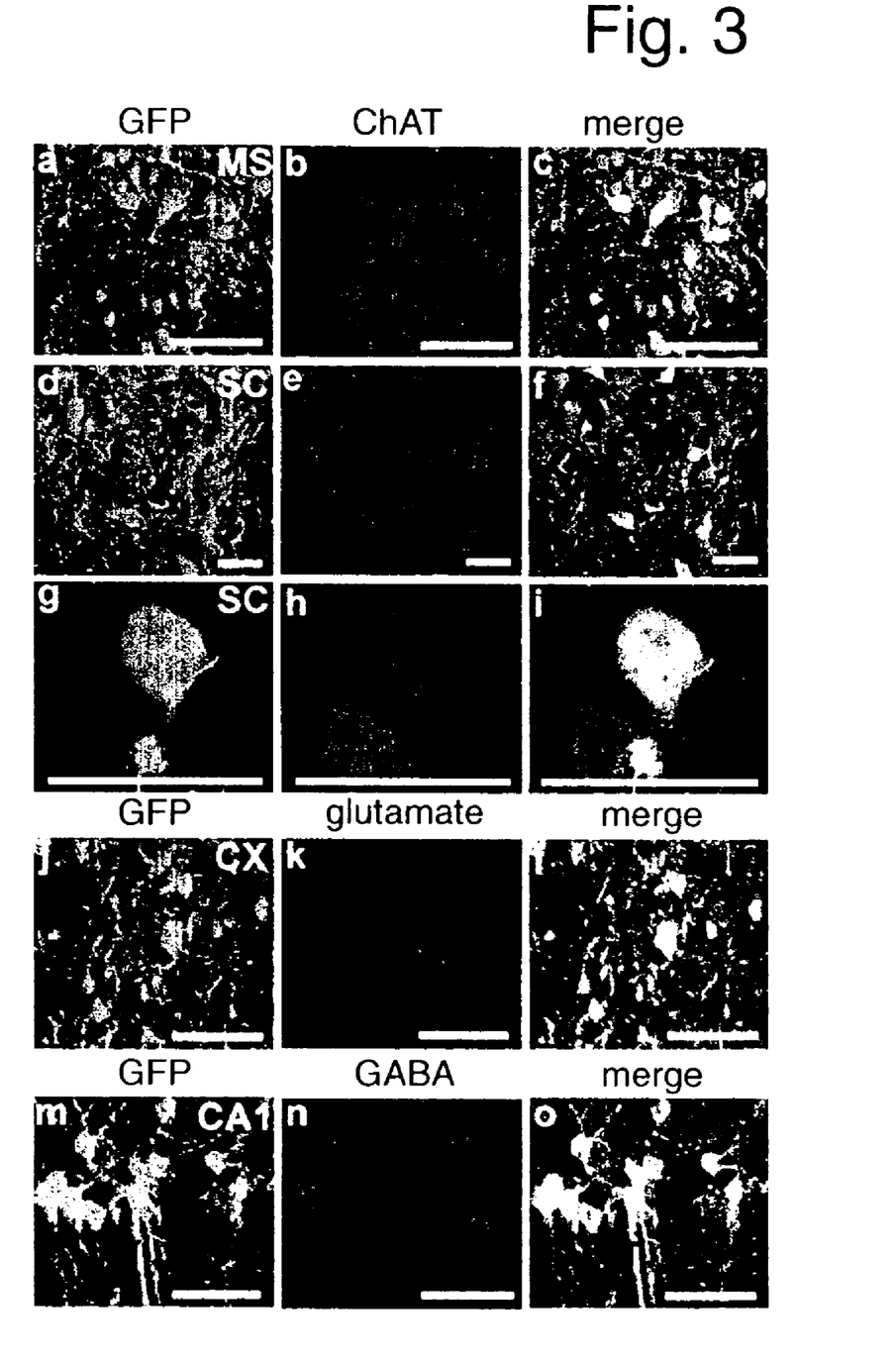
FIG. 3 shows region-specific differentiation of neuron subtypes from primed hNSCs after grafting in brain or spinal cord of adult rats.

To determine subtypes of hNSC-derived neurons in rat CNS, immunofluorescent analyses was performed using various specific antibodies. Single channel or merged confocal XY images with a Z thickness of either 1 μm or 0.3 μm are illustrated in FIG. 3. Many of the GFP+ neurons were double labeled with the ChAT specific antibody in medial septum (FIGS. 3a-c) and spinal cord (FIGS. 3d-f) of the host brain, which are regions containing many endogenous ChAT+ neurons. A few GFP+/ChAT+ double-labeled neurons were found in prefrontal cortex, an area with a limited number of endogenous ChAT neurons. No GFP+/ChAT+ neurons were detected in the hippocampus where no endogenous ChAT neurons are found. In the spinal cord, some transplanted ChAT neurons appeared to have size and morphology indistinguishable from endogenous a motoneurons (FIGS. 3g-i).

Immunohistochemical analyses with antibodies that specifically recognize other neuronal subtypes also revealed region-specific patterns. For example, glutamate immunoreactivity was found in the majority of GFP+ cells grafted into cortex (FIGS. 3j-l), some cells in spinal cord and the dentate gyrus of hippocampus, a few in medial septum, and none in the CA1 region of hippocampus (data not shown). In contrast, the majority of the grafted GFP+ cells in the CA1 region (FIGS. 3m-o) as well as some cells in all other regions tested (data not shown) were double labeled with a GABA antibody. No GFP+ cells were immunoreactive to a dopaminergic neuronal marker, tyrosine hydroxylase.

Figure 4:
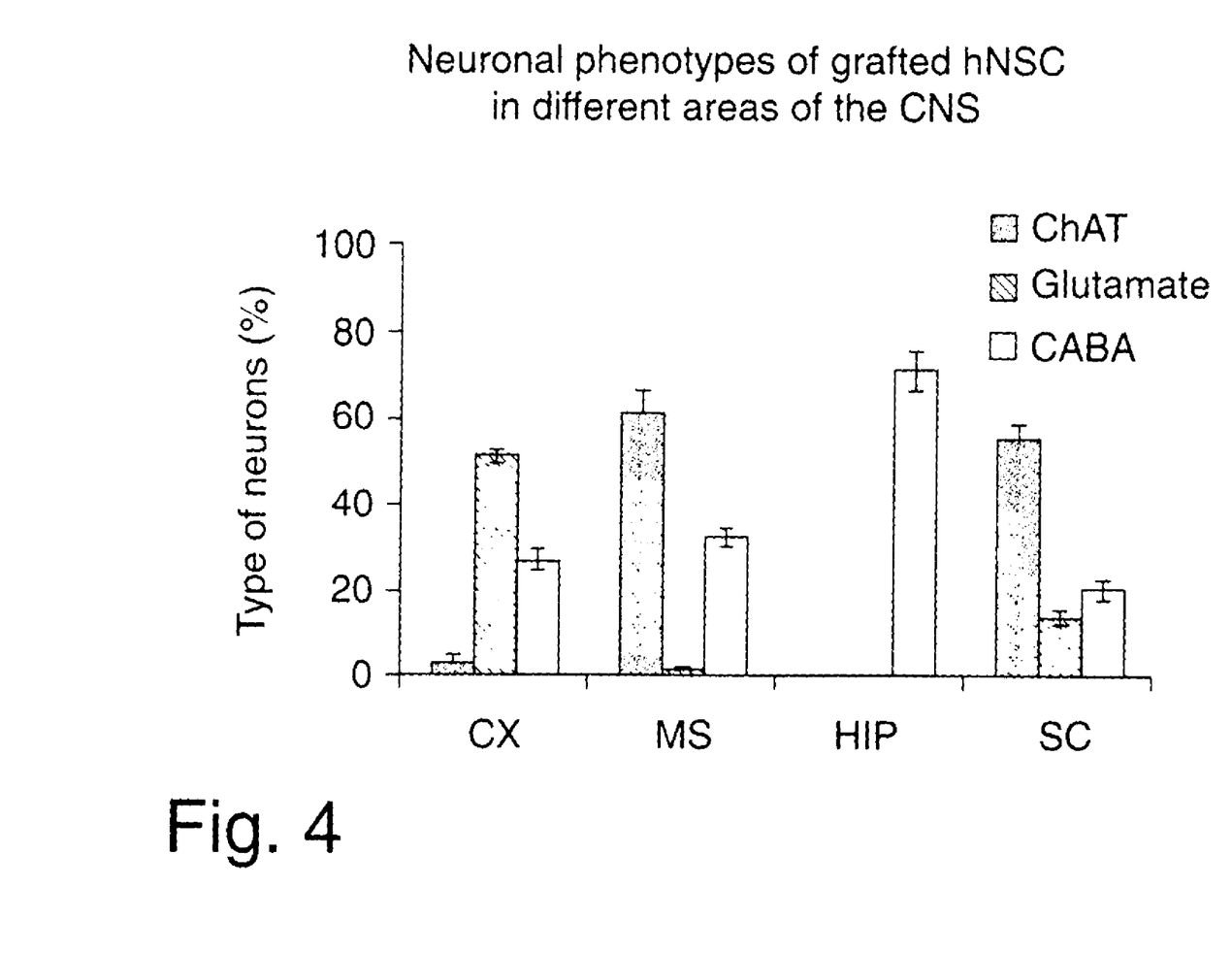

To quantify neuronal differentiation of grafted hNSCs, the number of GFP+ green cell profiles was counted, as well as of each phenotype described above. Approximately 20% and 6% of grafted cells (50,000 originally) survived in the host brain and spinal cord, respectively. 94.4 to 96.9% of the surviving GFP+ cells were differentiated into neurons as determined by TJU1 staining, while 3-5% became astrocytes. Since no significant differences were observed between FHL-primed and SFHL-primed hNSCs (n=5 for each region in each group), all ten animals for each region were pooled to obtain quantitative analyses of neuronal subtypes (ChAT, Glutamate or GABA) with the means (±s.e.m.) plotted in FIG. 4. Specifically, 61.3±5.4% and 55.5±3.2% of the GFP+ cells become cholinergic neurons when grafted in medial septum and spinal cord, respectively. hNSC-derived glutamatergic neurons were mainly detected in prefrontal cortex (51.1±1.5%), and in a much lower percentage (13.9±1.7%) in spinal cord. While 71.3±4.9% of GFP+ cells turned into GABAergic neurons in the CA1 region of hippocampus, smaller fractions (20-30%) of such neurons were observed in all other areas we transplanted. Thus, over 95% of the primed stem cells differentiated into neurons and 50-70% of the cells acquired a cholinergic phenotype identified by immunocytochemical staining with a specific antibody against choline acetyltransferase (ChAT). These findings represent a breakthrough in efforts to develop stem cell-based cell therapy for neurological diseases involving the loss of cholinergic neurons.

The in vivo transplantation data from this example indicate that both bFGF/heparin and adhesive culture play key roles in directing neuronal differentiation of hNSCs. It is known that bFGF under certain conditions favors neuronal differentiation. See Shihabuddin et al., *Arch. Neurol.* 1999; 56:29-32 and Whittemore et al., *Exp. Cell Res.* 1999; 252:75-95. Furthermore, heparin may potentiate the biological activity of bFGF through its helper effect on the binding of bFGF to its tyrosine kinase receptor. See Kan et al, *Science* 1993; 259: 1918-1921 and Fannon et al., Biochemistry 2000; 39:1434-1445. Lack of heparin, therefore, might contribute in part to the absence of neuronal differentiation from adult rat neural stem cells when they are transplanted into non-neurogenic spinal cord. Shihabuddin et al., *J. Neurosci.* 2000; 20:8727-8735 and Cao et al., *Exp. Neurol.* 2001; 167:48-58. Although underlying mechanisms remain to be defined, the bFGF/heparin treatment of adhesively cultured hNSCs for 6-7 days appears to prime stem cells evenly toward a plastic intermediate stage. They then differentiated into neurons and astroglial cells in vivo. A high percentage of the primed hNSCs develop into mature neurons with region-specific subtypes when grafted into either neurogenic or non-neurogenic areas in intact rat CNS.

Transplantation of Primed hNSCs into Rat Spinal Cord.

Figure 5:
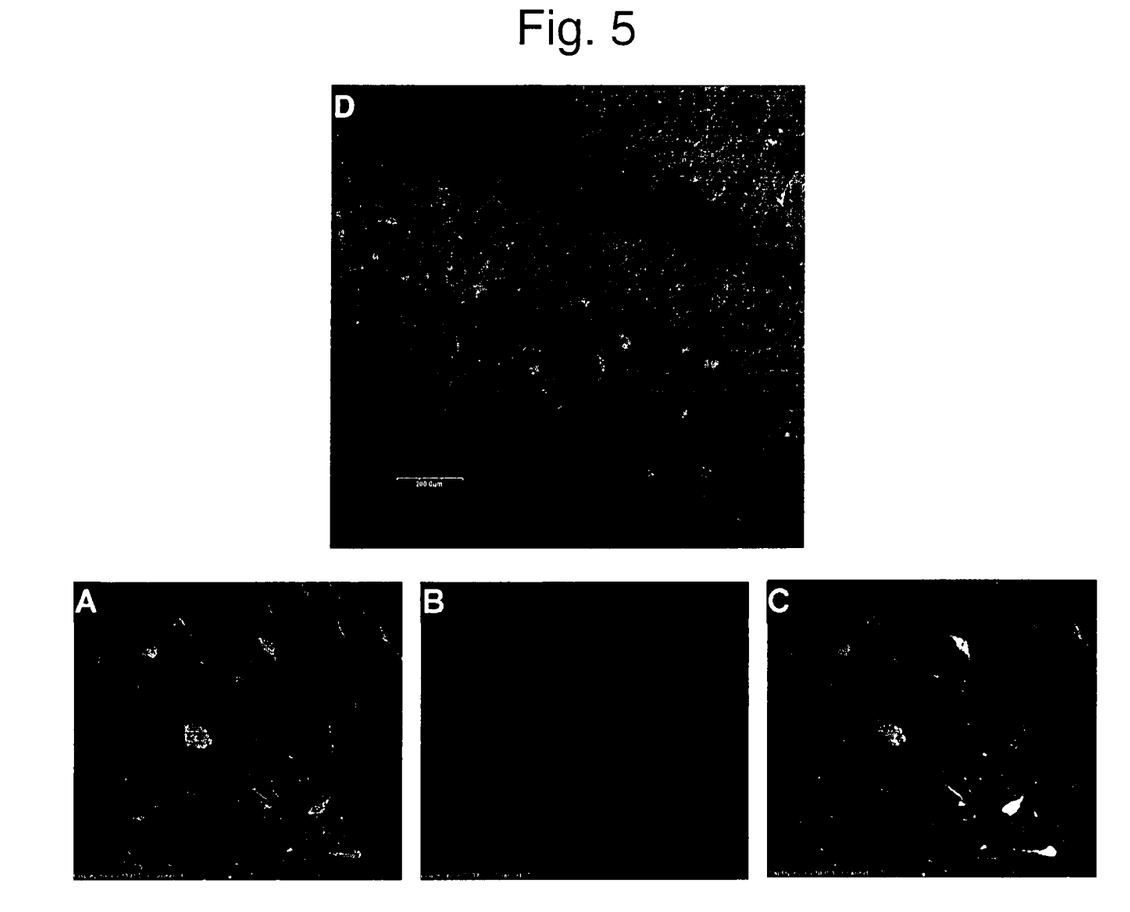
FIG. 5 shows immunofluorescent staining of hNSCs primed with Sonic hedgehog, hFGF, heparin and laminin one month after transplantation into adult rat spinal cord. Longitudinal sections were collected.

For the results shown in FIG. 5, of the transplantation of primed hNSCs into the spine, on the day of transplantation, animals were administered intraperitoneally (i.p.) with 10 mg/kg xylazine and 70 mg/kg ketamine for anesthesia. An antiseptic laminectomy was performed at L1 using the last rib as a reference. Under the assistance of an operation microscope, dura was incised after applying a small amount of 1% Lidocaine. The animal was placed onto a modified small animal spinal apparatus (David Kopf Instruments), with its dorsal spinous processes fixed by spine clamps. $0.5-1\times10^5$ cells/2 μl hNSCs were injected to the left side of spinal cord 0.7 mm from the midline and 1.0 mm in depth using a 5 μl Hamilton syringe with a 26 gauge needle. The injection speed was controlled by a microinjection unit (David Kopf Instruments) at 0.25 μl/min. The needle was held in place for 1 minute before gradually withdrawing. Fascia and muscles were sutured and the skin incision was closed with surgical stables. Animals were administered with 65,000 units sodium penicillin (i.m.) and 4 ml lactated Ringer's solution (i.p.), and kept on a thermopad until awake. Animals were kept on CsA for at least 1 month after transplantation.

At the different time points (2 weeks, 1 month), animals were treated with an overdose of sodium pentobarbital (i.p.) before intracardial perfusion at 65 ml/min with 0.1 M cold PBS and then 400 ml of ice-cold 4% paraformaldehyde in PBS, pH 7.4. A spinal cord fragment (1-2 cm in length) containing the graft was dissected, postfixed in 4% paraformaldehyde at 4° C. overnight, and then immersed in 30% sucrose until sunk (usually 2 days). Tissue blocks were embedded in OCT compound and frozen in liquid nitrogen-cooled isopentane. Serial longitudinal sections at a thickness of 32 μm were cut in a cryostat and immersed in ice-cold PBS until used.

Primed cells, pre-labeled with enhanced green fluorescent protein (EGFP) using an adeno-associated viral vector delivery system, were transplanted into adult rat spinal column. Cells were primed with Sonic hedgehog (Shh), basic fibroblast growth factor (bFGF), heparin, laminin, epidermal growth factor (EGF), retinoic acid (RA), neurotrophin 3 (NT-3) and/or neurotrophin 4 (NT-4). A priming procedure using a combination of Shh, bFGF, heparin and laminin produced large, neuronal-like cells. Other priming treatments produced predominantly small neurons. One month after transplantation, the animals were sacrificed and spinal cords were collected and subjected to immunofluorescence labeling using an antibody directly against choline acetyltransferase (ChAT), which is the enzyme producing acetylcholine. Using EGFP, transplanted hNSCs were easily identified by their green fluorescent labeling (FIG. 5). Fluorescent green labeling cells co-labeling with fluorescent red ChAT antibody (polyclonal anti-ChAT at 1:200 dilution) are cholinergic neurons of hNSCs origin (FIG. 5). Red-labeled neurons with no green labeling are most likely of host origin. In the multiple sections stained so far, a high percentage of double labeling, cholinergic neurons of hNSC origin are seen.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method of providing cholinergic neurons to a subject affected by a condition characterized by the loss of cholinergic neurons, the method comprising:
expanding human neural stem cells and/or progeny thereof by suspension culture as neurospheres in a serum-free mixture comprising epidermal growth factor, basic fibroblast growth factor and leukemia inhibitory factor (LIF);
adhesively culturing the expanded human neural stem cells and/or progeny thereof in vitro with a serum-free mixture comprising basic fibroblast growth factor, mammalian Sonic Hedgehog protein or an N-terminus-containing fragment thereof, laminin and heparin; and
implanting the adhesively cultured human neural stem cells and/or progeny thereof into the spinal cord or brain of the subject,
wherein the implanted adhesively cultured human neural stem cells and/or progeny thereof differentiate into cholinergic neurons and wherein the subject is affected with ALS or a spinal cord injury.

2. The method of claim 1 wherein the mixture for adhesive culturing comprises about 0.002 μg/ml to about 1.0 μg/ml Sonic Hedgehog protein or an N-terminus-containing fragment thereof.

3. A method of priming human neuronal stem cells to differentiate into specific neuronal phenotype, the method comprising:
expanding human neural stem cells and/or progeny thereof by suspension culture as neurospheres in a serum-free mixture comprising epidermal growth factor, basic fibroblast growth factor and leukemia inhibitory factor (LIF),
adhesively culturing said expanded human neuronal stem cells in vitro with a serum-free mixture comprising basic fibroblast growth factor, mammalian Sonic Hedgehog protein or an N-terminus-containing fragment thereof, heparin and an extracellular matrix component,
wherein said adhesively cultured human neuron stem cells differentiate into nestin negative, cholinergic neurons when implanted into the mammalian spinal cord.

4. The method of claim 3 wherein the serum-free mixture for adhesive culturing comprises:
up to about 20 ng/ml basic fibroblast growth factor,
about 0.5 μg/ml to about 5 μg/ml laminin, and
about 0.5 μg/ml to about 10 μg/ml heparin.

5. The method of claim 4 wherein the mixture for adhesive culturing comprises about 0.002 μg/ml to about 1.0 μg/ml Sonic Hedgehog protein or an N-terminus-containing fragment thereof.

6. The method of claim 3 wherein the mixture for adhesive culturing comprises about 0.002 μg/ml to about 1.0 μg/ml Sonic Hedgehog protein or an N terminus-containing fragment thereof.

7. The method of claim 3 wherein the neural stem cells and/or progeny thereof are multipotent stem cells, pluripotent stem cells, or combinations thereof.

8. The method of claim 3 wherein the neural stem cells and/or progeny thereof are derived from embryonic neural tissue, fetal neural tissue, adult neural tissue, or combinations thereof.

9. The method of claim 3 wherein the mixture for adhesive culturing comprises up to about 20 ng/ml basic fibroblast growth factor.

10. The method of claim 3 wherein the mixture for adhesive culturing comprises about 0.5 μg/ml to about 10 μg/ml heparin.

11. The method of claim 3 wherein the extracellular matrix component is selected from the group consisting of laminin, collagen, fibronectin and combinations thereof.

12. The method of claim 11 comprising about 0.5 μg/ml to about 5 μg/ml laminin.

13. The method of claim 3 wherein the neural stem cells and/or progeny thereof are cultured adhesively onto a fixed substrate selected from the group consisting of poly-D-lysine, poly-L-ornithine, laminin, matrigel, collagen and fibronectin.

14. The method of claim 3 wherein the neural stem cells and/or progeny thereof are adhesively cultured in vitro for about 5 to about 7 days prior to implanting.

15. A method of producing cholinergic neurons, the method comprising:
expanding human neural stem cells and/or progeny thereof by suspension culture as neurospheres in a serum-free mixture comprising epidermal growth factor, basic fibroblast growth factor and leukemia inhibitory factor (LIF);
adhesively culturing the expanded human neural stem cells and/or progeny thereof in vitro with a serum-free mixture comprising basic fibroblast growth factor, heparin, mammalian Sonic Hedgehog protein or an N-terminus-containing fragment thereof, and an extracellular matrix component; and implanting the adhesively cultured human neural stem cells and/or progeny thereof into the mammalian spinal cord or brain;

wherein the implanted adhesively cultured human neural stem cells and/or progeny thereof differentiate into cholinergic neurons.

16. The method of claim 15, wherein the mixture for adhesive culturing comprises:
up to about 20 ng/ml basic fibroblast growth factor,
about 0.5 µg/ml to about 5 µg/ml laminin, and
about 0.5 µg/ml to about 10 µg/ml heparin.

17. The method of claim 16 wherein the mixture for adhesive culturing comprises about 0.002 µg/ml to about 1.0 µg/ml Sonic Hedgehog protein or an N-terminus-containing fragment thereof.

18. The method of claim 15 wherein the neural stem cells and/or progeny thereof are multipotent stem cells, pluripotent stem cells, or combinations thereof.

19. The method of claim 15 wherein the neural stem cells and/or progeny thereof are derived from embryonic neural tissue, fetal neural tissue, adult neural tissue, or combinations thereof.

20. The method of claim 15 wherein the mixture for adhesive culturing comprises up to about 20 ng/ml basic fibroblast growth factor.

21. The method of claim 15 wherein the mixture for adhesive culturing comprises about 0.5 µg/ml to about 10 µg/ml heparin.

22. The method of claim 15 wherein the extracellular matrix component is selected from the group consisting of laminin, collagen, fibronectin and combinations thereof.

23. The method of claim 15 wherein the extracellular matrix component is laminin.

24. The method of claim 23 comprising about 0.5 µg/ml to about 5 µg/ml laminin.

25. The method of claim 15 wherein the neural stem cells and/or progeny thereof are cultured adhesively onto a fixed substrate selected from the group consisting of poly-D-lysine, poly-L-ornithine, laminin, matrigel, collagen and fibronectin.

26. The method of claim 15 wherein the neural stem cells and/or progeny thereof are adhesively cultured in vitro for about 5 to about 7 days prior to implanting.

27. The method of claim 15 wherein the mixture for adhesive culturing comprises about 0.002 µg/ml to about 1.0 µg/ml Sonic Hedgehog protein or an N terminus containing fragment thereof.

28. A method of producing cholinergic neurons, the method comprising:
expanding human neural stem cells and/or progeny thereof by suspension culture as neurospheres in a serum-free mixture comprising epidermal growth factor, basic fibroblast growth factor and leukemia inhibitory factor (LIF);
adhesively culturing the expanded human neural stem cells and/or progeny thereof in vitro with a serum-free mixture comprising basic fibroblast growth factor, mammalian Sonic Hedgehog protein or an N-terminus-containing fragment thereof, heparin and laminin; and
implanting the adhesively cultured human neural stem cells and/or progeny thereof into the mammalian spinal cord or medial septum;

wherein the implanted adhesively cultured human neural stem cells and/or progeny thereof differentiate into cholinergic neurons.

29. The method of claim 28 wherein the mixture for adhesive culturing comprises about 0.002 µg/ml to about 1.0 µg/ml Sonic Hedgehog protein or an N-terminus-containing fragment thereof.

30. A method of providing cholinergic neurons to a subject affected by a condition characterized by the loss of cholinergic neurons, the method comprising:
expanding human neural stem cells and/or progeny thereof by suspension culture as neurospheres in a serum-free mixture comprising epidermal growth factor, basic fibroblast growth factor and leukemia inhibitory factor (LIF);
adhesively culturing the expanded human neural stem cells and/or progeny thereof in vitro with a serum-free mixture comprising basic fibroblast growth factor, mammalian Sonic Hedgehog protein or an N-terminus-containing fragment thereof, laminin and heparin; and
implanting the adhesively cultured human neural stem cells and/or progeny thereof into the spinal cord or brain of the subject;

wherein the implanted adhesively cultured human neural stem cells and/or progeny thereof differentiate into cholinergic neurons.

31. The method of claim 30 wherein the mixture for adhesive culturing comprises about 0.002 µg/ml to about 1.0 µg/ml Sonic Hedgehog protein or an N terminus-containing fragment thereof.

32. The method of claim 30 wherein the neural stem cells and/or progeny thereof are multipotent stem cells, pluripotent stem cells, or combinations thereof.

33. The method of claim 30 wherein the neural stem cells and/or progeny thereof are derived from embryonic neural tissue, fetal neural tissue, adult neural tissue, or combinations thereof.

34. The method of claim 30 wherein the mixture for adhesive culturing comprises up to about 20 ng/ml basic fibroblast growth factor.

35. The method of claim 30 wherein the mixture for adhesive culturing comprises about 0.5 µg/ml to about 10 µg/ml heparin.

36. The method of claim 35 wherein the mixture for adhesive culturing comprises about 0.002 µg/ml to about 1.0 µg/ml Sonic Hedgehog protein or an N-terminus-containing fragment thereof.

37. The method of claim 30 wherein the extracellular matrix component is selected from the group consisting of laminin, collagen, fibronectin and combinations thereof.

38. The method of claim 37 comprising about 0.5 µg/ml to about 5 µg/ml laminin.

39. The method of claim 30, wherein the mixture for adhesive culturing comprises:
up to about 20 ng/ml basic fibroblast growth factor,
about 0.5 µg/ml to about 5 µg/ml laminin, and
about 0.5 µg/ml to about 10 µg/ml heparin.

40. The method of claim 30 wherein the neural stem cells and/or progeny thereof are cultured adhesively onto a fixed substrate selected from the group consisting of poly-D-lysine, poly-L-ornithine, laminin, matrigel, collagen and fibronectin.

41. The method of claim 30 wherein the neural stem cells and/or progeny thereof are adhesively cultured in vitro for about 5 to about 7 days prior to implanting.

* * * * *